(12) United States Patent
Maiefski

(10) Patent No.: US 6,358,414 B1
(45) Date of Patent: Mar. 19, 2002

(54) PRESSURE REGULATION APPARATUS AND METHOD FOR MULTIPLE CHANNEL HIGH THROUGHPUT PURIFICATION

(75) Inventor: Romaine Maiefski, Ocean Side, CA (US)

(73) Assignee: Ontogen Corporation, Carlsbad, CA (US)

( * ) Notice: Subject to any disclaimer, the term of this patent is extended or adjusted under 35 U.S.C. 154(b) by 0 days.

(21) Appl. No.: 09/569,377

(22) Filed: May 11, 2000

Related U.S. Application Data

(63) Continuation-in-part of application No. 09/430,194, filed on Oct. 29, 1999.

(51) Int. Cl.⁷ .............................................. B01D 15/08
(52) U.S. Cl. .................... 210/198.2; 210/656; 210/659; 210/137; 210/143; 137/334; 251/118; 251/265; 251/129.11; 251/129.12; 251/368
(58) Field of Search ................................ 251/118, 265, 251/129.11, 129.12, 368; 137/334; 210/635, 656, 659, 137, 143, 198.2; 95/82; 96/101; 422/70; 436/161

(56) References Cited

U.S. PATENT DOCUMENTS

| | | | | |
|---|---|---|---|---|
| 2,733,135 A | | 1/1956 | Huckabay | 23/230 |
| 3,250,395 A | | 5/1966 | Blume | 210/198.2 |
| 3,653,399 A | * | 4/1972 | Steele | 137/334 |
| 4,079,009 A | | 3/1978 | Seiler et al. | 210/198.2 |
| 4,448,684 A | * | 5/1984 | Paradis | 210/198.2 |

(List continued on next page.)

FOREIGN PATENT DOCUMENTS

| | | | | |
|---|---|---|---|---|
| SU | 940057 | | 6/1982 | 210/198.2 |
| WO | WO 98/35227 | | 8/1998 | 210/198.2 |

OTHER PUBLICATIONS

E. Von Arx, P. Richert, R. Stoll, K. Wagner, and Wuest, "New Aids for Preparative High–Performance Liquid Chromatography", Journal of Chromatography, 1982, vol. 238, pp. 419–425.

Michael J. Kessler, "Quantitation of Radiolabeled Biological Molecules Separated by High–Performance Liquid Chromatography", Journal of Chromatography, 1983, vol. 255, pp. 209–217.

Robert M. Campbell and Milton L. Lee, "Supercritical Fluid Fractionation of Petroleum– and Coal–Derived Mixtures", Anal. Chem., 1986, vol. 58, No. 11, pp. 2247–2251.

(List continued on next page.)

*Primary Examiner*—Ernest G. Therkorn
(74) *Attorney, Agent, or Firm*—Perkie Coie, LLP

(57) ABSTRACT

A pressure regulator assembly usable in, as an example, a multiple channel high throughput purification system. The pressure regulator assembly includes an inlet line and an outlet line connectable to a fluid channel. A regulator body has a regulator inlet connected to the inlet line and a regulator outlet connected to the outlet line. The regulator body has a chamber therein in fluid communication with the regulator inlet and outlet. A nozzle is in fluid communication with the regulator inlet and has a nozzle outlet adjacent to the chamber. A stem is axially aligned with the nozzle outlet and has a regulating surface adjacent to the nozzle outlet to restrict the fluid flow through the chamber to the regulator outlet. A mounting rod is attached to a mounting portion on the stem. The mounting rod and stem are axially moveable in the regulator body relative to the nozzle outlet. An adjustment member is connected to the mounting rod and is axially moveable to adjust the position of the stem relative to the nozzle outlet. The adjustment mechanism has a dual concentric thread arrangement with first and second threads thereon configured to provide an attenuated movement of the stem's regulating surface relative to the nozzle outlet to selectively adjust a pressure of the fluid flow in the chamber. A drive mechanism is connected to the adjustment member and positioned to rotate the adjustment member for axial adjustment of the stem relative to the nozzle outlet for pressure control of the fluid flow.

35 Claims, 25 Drawing Sheets

U.S. PATENT DOCUMENTS

| | | | |
|---|---|---|---|
| 4,554,071 A | 11/1985 | Ruijten et al. | 210/198.2 |
| 4,719,011 A | 1/1988 | Shalon et al. | 210/198.2 |
| 4,766,082 A | 8/1988 | D'Autry | 436/178 |
| 4,787,971 A | 11/1988 | Donald | 210/198.2 |
| 4,828,219 A * | 5/1989 | Ohmi | 251/118 |
| 4,911,405 A * | 3/1990 | Weissgerber | 251/368 |
| 5,009,778 A | 4/1991 | Nickerson et al. | 210/198.2 |
| 5,143,118 A | 9/1992 | Sule | 137/554 |
| 5,151,178 A | 9/1992 | Nickerson et al. | 210/198.2 |
| 5,234,599 A | 8/1993 | Cortes et al. | 210/659 |
| 5,413,311 A * | 5/1995 | Arstein | 251/331 |
| 5,433,244 A | 7/1995 | Sule | 137/554 |
| 5,494,258 A * | 2/1996 | Weissgerber | 251/368 |
| 5,605,317 A | 2/1997 | Mealy et al. | 251/129.01 |
| 5,614,089 A * | 3/1997 | Allington | 210/198.2 |
| 5,657,962 A | 8/1997 | Neron et al. | 251/129.15 |
| 5,669,406 A | 9/1997 | Gluf, Jr. | 137/270 |
| 5,670,054 A | 9/1997 | Kibbey et al. | 210/656 |
| 5,749,969 A | 5/1998 | Kobak et al. | 118/319 |
| 5,782,267 A | 7/1998 | Yoo | 137/596.17 |
| 5,899,437 A | 5/1999 | Quarre | 251/129.2 |
| 5,938,932 A | 8/1999 | Connelly et al. | 210/659 |
| 6,007,046 A | 12/1999 | Rothermel | 251/129.17 |
| 6,080,318 A * | 1/2000 | Gumm | 210/659 |
| 6,054,047 A * | 4/2000 | Hindsgaul | 210/198.2 |
| 6,068,010 A | 5/2000 | Reinicke | 137/1 |
| 6,090,280 A * | 7/2000 | Connelly | 210/198.2 |
| 6,102,068 A | 8/2000 | Higdon et al. | 13/341 |
| 6,120,003 A | 9/2000 | Lubischer et al. | 251/129.02 |
| 6,126,140 A | 10/2000 | Johnson et al. | 251/129.01 |
| 6,164,323 A | 12/2000 | Smith et al. | 137/554 |
| 6,197,198 B1 * | 3/2001 | Messinger | 210/656 |
| 6,210,571 B1 * | 4/2001 | Zambias | 210/198.2 |

OTHER PUBLICATIONS

Johan Uusijarvi, Borje Egestad, and Jan Sjovall, "Manual and Automated Enrichment Procedures for Biological Samples using Lipophilic Gels", Journal of Chromatography, 1989, vol. 488, pp. 87–104.

Tooru Imahashi, Yoshio Yamauchi, and Munco Saito, "Fractionation and Identification of Additives in Polyvinylchloride Film by Supercritical Fluid Extraction/Semi–Preparative Supercritical Fluid Chromatography", Bunseki Kagaku, 1990, vol. 39, pp. 79–85.

Hans M.H. van Eijk, Mark P.L. Huinck, Dennis R. Rooyakkers, and Nicolaas E.P. Deutz, "Automated Simultaneous Isolation and Quantitation of Labeled Amino Acid Fractions From Plasma and Tissue by Ion–Exchange Chromatography", Journal of Chromatography B, 1994, vol. 660, pp. 251–257.

John F. Cargill and Romaine R. Maiefski, "Automated Combinatorial Chemistry on Solid Phase", Laboratory Robotics and Automation, 1996, vol. 8, pp. 139–148.

Robert Pal, Kristina Tolvaj, and Miklos Juhasz, "Separation of Gas Oil Samples by Coupled Packed and Open Tubular Column SFC", J. Microcolumn Separations, 1996, vol. 8, pp. 269–273.

Bradley L. Ackermann and Brian T. Regg, "Rapid Analysis of Antibiotic–Containing Mixtures From Fermentation Broths by Using Liquid Chromatography–Electrospray Ionization–Mass Spectrometry and Matrix–Assisted Laser Desorption Ionization–Time–of–Flight–Mass Spectrometry", Journal of the American Society of Mass Spectrometry, 1996, vol. 7, pp. 1227–1237.

Donald J. Daley, Russel D. Scammell, David James, Iain Monks, Roberto Raso, Alison E. Ashcroft, and Aaron J. Hudson, "High–Throughput LC–MS Verification of Drug Candidates From 96–Well Plates", Am. Biotechnol. Lab., Nov. 1997, vol. 15, pp. 24, 26, and 28.

Christopher E. Kibbey, "An Automated System for the Purification of Combinatorial Libraries by Preparative LC/MS", Laboratory Robotics and Automation, 1997, vol. 9, pp. 309–321.

L. Zeng, L. Burton, K. Yung, B. Shushan, and D.B. Kassel, "Automated Analytical/Preparative High–Performance Liquid Chromatography–Mass Spectrometry System for the Rapid Characterization and Purification of Compound Libraries", Journal of Chromatography A, Jan. 23, 1998, vol. 794, Nos. 1 and 2, pp. 3–13.

Chemical Abstracts, vol. 128, No. 13, Mar. 30, 1998, Angelika Weber, Holger Theils, and Reza Hashemi, "Automated and Flexible Chromatographic Purification. Part 2. Experiences in the Operational Phase", p. 1320, Col. 2, Abstract No. 162374p, LaborPraxis, 1998, 22(1), 43–44.

Chemical Abstracts, vol. 129, No. 7, Aug. 17, 1998, Jeffrey Kiplinger et al., "Structure–Controlled Automated Purification of Parallel Synthesis Products in Drug Discovery", p. 655, Col. 2, Abstract No. 81293e, Rapic Commun. Mass Spectrom., 1998, 12(10), 658–664.

T. Wang, L. Zeng, T. Strader, L. Burton, and Daniel B. Kassel, "A New Ultra–High Throughput Method for Characterizing Combinatorial Libraries Incorporating a Multiple Probe Autosampler Coupled with Flow Injection Mass Spectrometry Analysis", Rapid Commun. Mass Spectrom., 1998, vol. 12, pp. 1123–1129.

Lu Zeng and Daniel B. Kassel, "Developments of a Fully Automated Parallel HPCL/Mass Spectrometry System for the Analytical Characterization and Preparative Purification of Combinatorial Libraries", Anal. Chem., 1998, vol. 70, pp. 4380–4388.

F. Vérillon, D. Heems, B. Pichon, K. Coleman, and J.–C. Robert, "Supercritical fluid chromatography With Independent Programming of Mobile–Phase Pressure, Composition, and Flow Rate", American Laboratory, Jun. 1992, 8 pages.

M. Ashraf–Khorassani, M.B. Gandee, M.T. Combs, and L. T. Taylor, "Semipreparative Separation and Fractionation of Sulfonamides via Supercritical Fluid Chromatography", Journal of Chromatographic Science, vol. 35, Dec. 1997, pp. 593–597.

"Gilson Supercritical Fluid Chromatography", booklet reproducing chapter entitled "Analytical and Preparative Carbon Dioxide Chromatography with Automated Pressure Control and Different Detectors" by Francis Vérillon and Keith Coleman, from the Marcel Dekker, Inc. book entitled "Supercritical Fluid Chromatography with Packed Columns: Techniques and Applications", edited by Klaus Anton and Claire Berger, France, Reference 800347A, May 1998, pp. 1–49.

* cited by examiner

PRESSURE REGULATION APPARATUS AND METHOD FOR MULTIPLE CHANNEL HIGH THROUGHPUT PURIFICATION

CROSS REFERENCE TO RELATED APPLICATION

This application is a continuation-in-part application to U.S. patent application Ser. No. 09/430,194 entitled "Apparatus and Method for Multiple Channel High Throughout Purification," filed Oct. 29, 1999.

TECHNICAL FIELD

The present invention is directed to pressure regulation apparatus and methods, usable in, as an example, sample purification, and more particularly, to pressure regulation apparatus and methods usable in, as an example, high throughput purification of samples from a chemical library.

BACKGROUND OF THE INVENTION

The relationship between structure and functions of molecules is a fundamental issue in the study of biological and other chemistry-based systems. Structure-function relationships are important in understanding, for example, the function of enzymes, cellular communication, cellular control and feedback mechanisms. Certain macromolecules are known to interact and bind to other molecules having a specific 3-dimensional spatial and electronic distribution. Any macromolecule having such specificity can be considered a receptor, whether the macromolecule is an enzyme, a protein, a glycoprotein, and antibody, or an oglionucleotide sequence of DNA, RNA, or the like. The various molecules which bind to receptors are known as ligands.

A common way to generate ligands is to synthesize molecules in a stepwise fashion in a liquid phase or on solid phase resins. Since the introduction of liquid phase and solid phase synthesis methods for peptides, oglionucleotides, and small organic molecules, new methods of employing liquid or solid phase strategies have been developed that are capable of generating thousands, and in some cases even millions of individual compounds using automated or manual techniques. A collection of compounds is generally referred to as a chemical library. In the pharmaceutical industry, chemical libraries of compounds are typically formatted into 96-well microtiter plates. This 96-well formatting has essentially become a standard and it allows for convenient methods for screening these compounds to identify novel ligands for biological receptors.

Recently developed synthesis techniques are capable of generating large chemical libraries in a relatively short period of time as compared to previous synthesis techniques. As an example, automated synthesis techniques for sample generation allows for the generation of up to 4,000 compounds per week. The samples, which contain the compounds, however, typically include 20%–60% impurities in addition to the desired compound. When samples having these impurities are screened against selected targets, such as a novel ligand or biological receptors, the impurities can produce erroneous screening results. As a result, samples that receive a positive result from initial screening must be further analyzed and screened to verify the accuracy of the initial screening result. This verification process requires that additional samples be available. The verification process also increases the cost and time required to accurately verify that the targeted compound has been located.

Samples can be purified in an effort to achieve an 85% purity or better. Screening of the purified samples provides more accurate and meaningful biological results. Conventional purification techniques, however, are very slow and expensive. As an example, conventional purification techniques using high pressure liquid chromatography (HPLC) take approximately 30 minutes to purify each sample. Therefore, purification of the 4,000 samples generated in one week would take at least 2,000 hours (i.e. 83.3 days or 2.77 months).

Conventional purification techniques, such as HPLC, also require large volumes of solvents and result in large volumes of waste solvent. Disposal of the solvents, particularly halogenated solvents, must be carefully controlled for legal and environmental reasons, so the disposal process can be laborious and very costly. Disposal of non-halogenated solvents is less rigorous. Accordingly, when halogenated and non-halogenated solvents are used, the waste solvents are separated. The separation process of large volumes of solvents, however, can be a difficult process to perform efficiently and inexpensively. Accordingly, purification of large chemical libraries can be economically prohibitive. Therefore, there is a need for a faster and more economical manner of purifying samples of large chemical libraries.

Supercritical fluid chromatography (SFC) provides faster purification techniques than HPLC. SFC utilizes a multiphase flow stream that includes a gas, such as carbon dioxide, in a supercritical state, a carrier solvent and a selected sample. The flow stream passes through a chromatography column, and is then analyzed in an effort to locate target compounds. SFC is beneficial because the solvent and sample are carried by the gas and the amount of solvent needed during a purification run is substantially less than the volume used in HPLC. Also, the amount of waste solvent at the end of a run is substantially less, so less waste solvent needs to be handled. SFC, however, requires pressure and temperature regulation that is difficult to control accurately and reliably long term.

There are many different configurations of the purification instruments. They typically share commonality in the concept wherein that samples are delivered to a chromatography instrument where compounds are separated in time, and a fraction collector collects the target compound. In order for these instruments to maintain the high throughput process, the instruments must be able to handle large sample numbers, as well as large samples in terms of mass weight and solvent volume. Tradition would specify the use of a semiprep or prep scale chromatography system for a typical milligram synthesis. While this is achievable, it has a low feasibility in a high throughput environment because several issues become apparent in such practice: large solvent usage, generation of large amounts of solvent waste, expensive large-bore columns, and relatively large collection volumes of target compounds. If the proper flow rate or column size is not used, sufficient chromatographic purity will not be achieved.

Further drawbacks experienced with high throughput purification techniques include durability of components to accommodate the high pressures, high volumes, or high flow rates of samples through the purification system. The purification system requires extreme accuracy and very high tolerances to avoid cross-contamination and to ensure purified compounds. The system components, thus, must be sufficiently durable to accept the aggressive environment while still providing the accurate results required. If the components are not sufficiently durable and they break or require repair too quickly, the purification system must be taken out of service to replace or repair the components.

Conventional SFC systems expose its components to extremely hostile environments at high pressures. The high pressures must be accurately controlled and maintained, typically by pressure regulators. The extremely erosive nature of the environment, however, can ruin valving components in the regulator. As a result, manufacturers have made the valving components out of very hard and erosion-resistant materials. In high pressure environments, however, the hard materials are brittle, fragile, and susceptible to breaking or cracking. The valving components are also exposed to cold temperatures due to the high pressure gas. As a result, the valving components can ice up, which can compromise the accuracy of the pressure regulation.

The pressure regulators of the high pressure systems must also be able to move the valving components very quickly and accurately for acceptable pressure control. The electromagnetic control mechanisms have been used for moving the valving components. Such mechanisms are typically large and have unswept dead volumes that can retain portions of the samples passing through the system. This unswept dead volume can result in cross-contamination between samples by sample carry-over or sample tailing. These mechanisms for controlling the valving mechanisms also experience difficulties in controlling the speed and velocity of the moving components so as to avoid accidental damage to the mechanisms. Accordingly, there is a need for pressure regulating devices usable in highly erosive, high pressure environments that achieve sufficient accuracy, control and durability.

A further drawback experienced in conventional purification processes of large chemical libraries includes sample management during the purification process. As an example, the chemical libraries are typically maintained in sets of 96-well microtiter plates, wherein each well includes a separate sample. Each sample is carefully tracked by its "well address" within the microtiter plate. When a sample or portion of a sample is removed for purification from a selected well of a microtiter plate, the purified sample is typically collected in a separate container, processed, and eventually returned to a receiving well in a similar microtiter plate. That receiving well preferably has a corresponding well address in the microtiter plate so as to maintain the accuracy of the library records regarding sample location in the respective microtiter plate.

Conventional purification processes typically require the reformatting of a purified sample because the large collected volumes of fluid (e.g., the solvent that contains the purified sample) is greater than the volume of a receiving well in a conventional microtiter plate. The large collected volumes must be reduced a volume that fits into the microtiter plate's well. The reduced volume of fluid containing the purified sample is also tracked and deposited into the appropriate well of the receiving microtiter plate that correctly maps to the well location from which the sample was taken at the start of the purification run. Such reformatting of purified samples into the receiving microtiter plate increases the time requirements and cost of the purification processes. Therefore, there is a need for a purification process that allows for quick and economical purification of samples that result in purified samples being collected directly to microtiter plates mapped directly to the original plate.

SUMMARY OF THE INVENTION

The present invention is directed to pressure regulation apparatus and methods, usable for multiple channel high throughput purification of samples from a chemical library that overcome drawbacks experienced in the prior art. In an illustrated embodiment utilizing a pressure regulation apparatus in accordance with the present invention, the method of multiple channel high throughput purification simultaneously purifies a plurality of samples, such as four samples, from a chemical library.

The purification process includes simultaneously purifying by supercritical fluid chromatography (SFC) all four samples in four channels of a purification system. The method includes passing a first sample along a SFC flow path of the first channel, separating the first sample into sample portions, spacing the sample portions apart from each other along at least a portion of the first fluid path. The pressure of the supercritical fluid in the flow stream is regulated with a back pressure regulator and a pressure relief valve in accordance with an embodiment of the present invention. The method also includes moving the separated sample portions along the fluid path, and detecting at least one sample portion flowing along the fluid path. The method further includes diverting a sampling away from the sample portion, directing the sampling to an analyzer while the remainder of the sample portion continues along the fluid path, analyzing the sampling with the analyzer, and determining if the one sample portion has selected sample characteristics. The method also includes collecting the one sample portion in a first receptacle, such as a well of a first microtiter plate, only if the sample portion has the selected sample characteristics. If the sample portion does not have the selected sample characteristics, the sample portion is collected in a second receptacle, such as a corresponding well in a second microtiter plate.

The multiple channel high throughput purification method of this illustrated embodiment further includes purifying a second sample along a second channel substantially simultaneously with the purification of the first sample. Purifying the second sample includes passing the second sample along a second flow path of the second channel, separating the second sample into sample portions, and spacing the sample portions apart from each other along at least a portion of the second fluid path with a pressure regulating assembly in accordance with an embodiment of the present invention. The method also includes moving the separated sample portions along the second fluid path, and detecting at least one of the sample portions flowing along the second fluid path. The method includes regulating the second sample's pressure along the flow path with a pressure regulating assembly in accordance with an embodiment of the present invention. The method further includes taking a sampling from the one sample portion and directing the sampling to the same analyzer used for the first channel. The remainder of the sample portion continues to flow along the second fluid path.

The method also includes analyzing the second sampling with the analyzer, wherein the first and second samplings are analyzed separately in accordance with a selected analysis priority protocol. The analysis of the second sampling determines if the sample portion has selected sample characteristics. The method further includes collecting the sample portion in a separate receptacle, such as a separate well in the first microtiter plate identified above, only if the sample portion has the second selected sample characteristics. If the sample portion does not have the selected sample characteristics, the sample portion is collected in another receptacle, such as a separate well in the second microtiter plate identified above.

In one embodiment of the invention, the method of high throughput purification includes purifying third and fourth samples along corresponding third and fourth channels in a manner similar to the purification discussed above regarding the first and second samples. In this embodiment, the same analyzer is used to analyze samplings from all four samples. The samplings are all analyzed separately and in accordance with the selected analysis priority protocol.

The invention is also directed to a pressure regulating assembly usable in one embodiment in a multiple channel high throughput purification system for substantially simultaneously purifying a plurality of samples from a chemical library. In one illustrated embodiment, the system includes a controller and a sample analyzer coupled to the controller, wherein the analyzer is configured to determine whether the samplings have elected sample characteristics. First, second, third, and fourth purification channels are coupled to the sample analyzer. The first purification channel includes a separation device positioned to receive a sample flow and to separate a first sample into sample portions so the ample portions are spaced apart from each other in the sample flow. A detector is positioned to receive the sample flow from the separation device and to detect at least one ample portion within the first sample. An adjustable back pressure regulator assembly receives the flow stream from the detector and controls the pressure of the flow stream within the first channel in accordance with an embodiment of the present invention.

In one embodiment of the invention, a pressure regulator assembly is provided for use in a high throughput fluid system having a fluid channel for carrying a fluid flow therethrough. The pressure regulator assembly includes an inlet line and an outlet line connectable to the fluid channel. A regulator body has a regulator inlet and outlet with the regulator inlet being connected to the inlet line and the regulator outlet being connected to the outlet line. The regulator body has a chamber therein in fluid communication with the regulator inlet and outlet. A nozzle is in fluid communication with the regulator inlet. The nozzle has a nozzle outlet adjacent to the chamber. A stem is axially aligned with the nozzle outlet. The stem has one end forming a regulating surface and another end forming a mounting portion. The regulating surface is positioned adjacent to the nozzle outlet and being positioned to restrict the fluid flow through the chamber to the regulator outlet.

The pressure regulator assembly in this embodiment also includes a mounting rod attached to the stem's mounting portion. The mounting rod and stem are axially moveable in the regulator body relative to the nozzle outlet. An adjustment member is connected to the mounting rod and is axially moveable to adjust the position of the stem relative to the nozzle outlet. The adjustment mechanism has a dual concentric thread arrangement with first and second threads thereon. The first threads engage the mounting rod and are configured to move the mounting rod and stem as a unit in a first direction and at a first rate relative to the nozzle outlet. The second threads are configured to move the adjustment member, the mounting rod, and the stem as a unit in a second direction and at a second rate relative to the nozzle outlet. The second direction being opposite the first direction, and the first rate being different than the second rate, to provide an attenuated movement of the stem's regulating surface relative to the nozzle outlet to selectively adjust a pressure of the fluid flow in the chamber. A drive mechanism is connected to the adjustment member and positioned to rotate the adjustment member for axial adjustment of the stem relative to the nozzle outlet for pressure control of the fluid flow. The pressure regulator assembly provides for highly accurate pressure control with virtually no dead volume that could result in cross-contamination between samples.

A microsampling device is positioned to receive the sample flow from the back pressure regulator and is moveable between open and closed positions while allowing a substantially continuous flow stream to pass through the device. In the closed position, the microsampling device blocks the flow stream from passing to the analyzer and allows the flow stream to continue to flow through the device. In the closed position, the microsampling device also allows a substantially continuous flow of carrier fluid to pass therethrough to the analyzer. In the open position, the microsampling device directs a sampling of at least the one sample portion to the analyzer for analysis, while a remainder of the one sample portion in the sample flow moves substantially uninterrupted through the microsampling device.

A pressure relief valve assembly, which in an embodiment is similar to the back pressure regulator, receives the remainder sample flow from the microsampling device and maintains a selected pressure in the sample flow downstream of the microsampling device. A flow directing valve is in fluid communication with the first flow path and is positioned to receive the sample flow downstream of the pressure relief valves. The flow directing valve is moveable to a first position to direct the one sample portion in one direction if the analyzer has determined that the one sample portion has the selected sample characteristics. The flow directing valve is moveable to a second position to direct the one sample portion in another direction if the analyzer has determined that the one sample portion does not have the selected sample characteristics. A first receptacle, such as a well of a microtiter plate, is positioned to receive the one sample portion from the flow directing device when the flow directing device is in the first position because the sample portion has the selected characteristics. A second receptacle, such as a well in a second microtiter plate, is positioned to receive the one sample portion when the flow directing device is in the second position because the sample portion does not have the selected characteristics.

The second purification channel of the purification system includes a separation device positioned to receive a second sample flow and to separate a second sample into sample portions. A separate detector is coupled to the separation device and is positioned to receive the second sample from the separation device. The detector is configured to detect at least one of the sample portions within the sample flow. A microsampling device is positioned to receive the sample flow from the detector and is moveable between open and closed positions. When the microsampling device is in the closed position, the microsampling device allows the second sample flow to pass therethrough and blocks the flow from passing to the analyzer. In the open position, the microsampling device directs a sampling of the one sample portion to the analyzer for analysis, while the remainder of the sample portion continues along the second flow path substantially uninterrupted.

A back pressure regulator and a pressure relief valve receive the second sample flow upstream and downstream, respectively, of the microsampling device to selectively control the pressure of the second sample flow along the second purification channel. A flow directing valve is in fluid communication with the second flow path and is positioned to receive the sample flow therethrough. The flow directing valve is moveable to a first position to direct the one sample portion in one direction if the analyzer has determined the sample portion has the selected sample characteristic. The flow directing valve is moveable to a second position to direct the one sample portion in another direction if the analyzer has determined that the sample portion does not have the selected sample characteristics. A waste receptacle receives the remainder of the flow that does not include the sample portion.

A receptacle, such as a separate well in the first microtiter plate, is positioned to receive the sample portion from the flow directing device when the flow directing device is in the first position because the sample portion has the selected characteristics. Another receptacle, such as a separate well in the second microtiter plate, is positioned to receive the sample portion when the flow directing device is in the second position because the sample portion does not have the selected characteristics.

In one embodiment of the invention, the purification system includes third and fourth purification channels that purify third and fourth samples substantially simultaneous with the purification of the first and second samples. Each of the third and fourth purification channels are coupled to the same analyzer and direct the sample portions to receptacles, such as wells in the first and second microtiter plates, discussed above.

An aspect of the invention provides a microsample or flow splitter valve for use in the high throughput purification system for purifying a selected sample from a chemical library. The purification system has a sample flow path, a carrier fluid flow path, and a sample analyzer in fluid communication with the sample and carrier flow paths. The microsample valve includes a valve body having an interior chamber therein, and sample flow inlet and outlet ports in fluid communication with the sample flow path and with the interior chamber. The valve body has a carrier fluid flow port in fluid communication with the carrier fluid flow path, and an outflow port channel in fluid communication with the analyzer. A stem is slidably disposed in the interior chamber and is moveable between first and second positions within the chamber. The stem has a fluid bypass channel that communicates with the sample inlet port and the outflow port when in the first position to allow a selected portion of the sample to flow to the analyzer. The stem blocks the carrier flow port when in the first position to prevent fluid from the carrier fluid flow path from moving into the outflow port.

The fluid bypass channel in the stem communicates with the carrier flow port and with the outflow port when in the second position to allow selected carrier fluid to flow through the valve body to the analyzer. The stem blocks the sample flow inlet port from communicating with the outflow port when in the second position to prevent the sample flow from flowing to the outflow channel.

An aspect of the invention also includes an automated fraction collection assembly that retains the microtiter plates in a fixed position and dispenses the sample portions into the selected wells in the microtiter plates. The fraction collection assembly includes a dispensing needle through which the sample portion is dispensed into disposable expansion chambers and then into the microtiter plate. The dispensing needle is mounted on a dispensing head adapted to extend into a disposable expansion chamber into which the sample portion is condensed and then dispensed into the microtiter plate.

The dispensing head is moveable from a pick-up position, where the expansion chambers are picked up, to a collection position over the microtiter plates, where the sample portions are dispensed into the selected well of the microtiter plate. The dispensing head is also moveable from the dispensing position to a chamber drop-off position, where the expansion chambers are released into a waste receptacle, so the dispensing needles are exposed. The dispensing head is further moveable to a wash position at a wash station on the fraction collection assembly, where the dispensing needles are washed to avoid cross-contamination between samples.

DETAILED DESCRIPTION OF THE INVENTION

The structure and fiction of exemplary embodiments of the present invention can best be understood by reference to the drawings. The same reference numbers may appear in multiple figures. The reference numbers refer to the same or corresponding structure in those figures.

Figure 1:
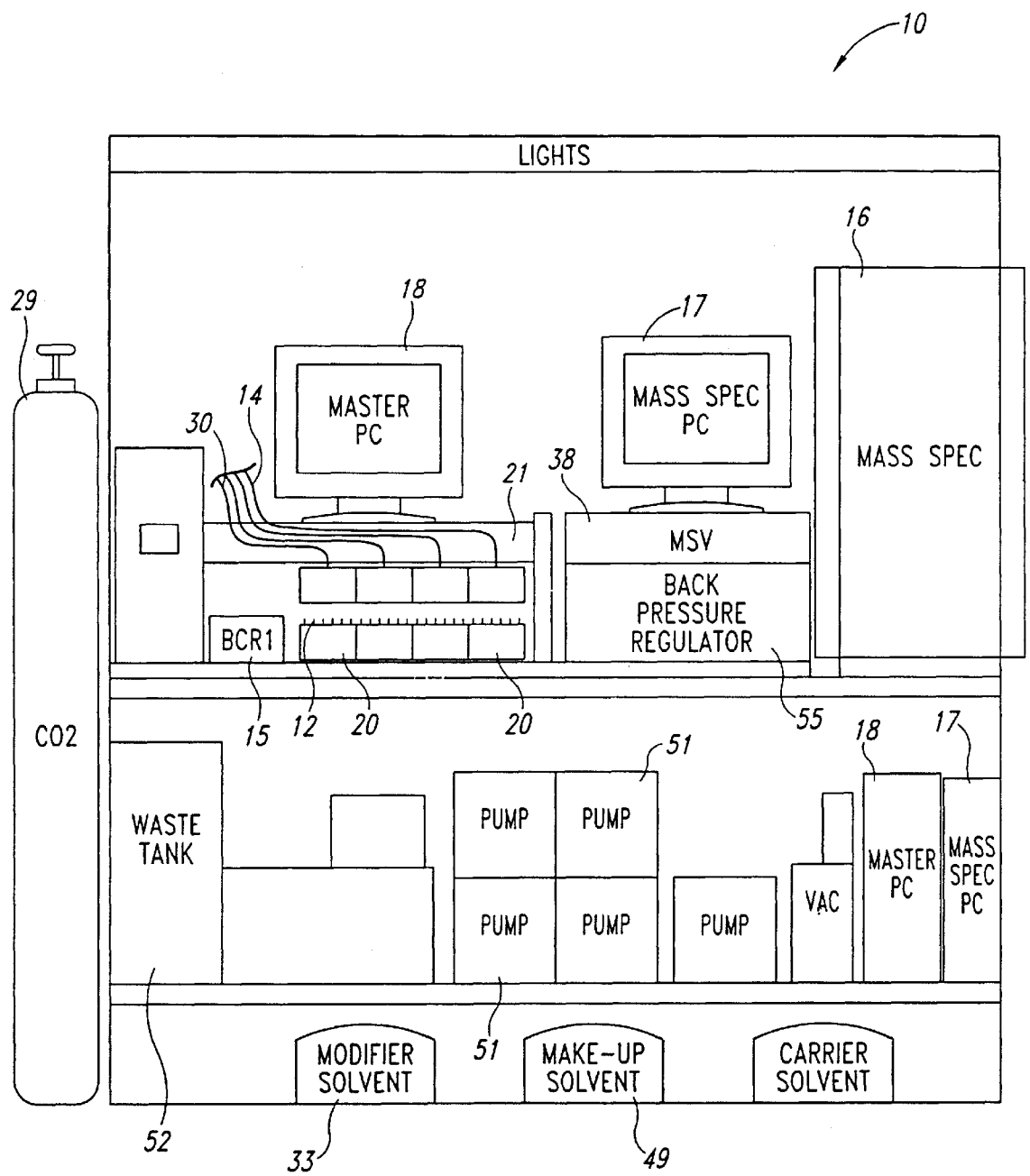
FIG. 1 is a schematic view of one portion of a multiple channel high throughput purification system with pressure regulator assemblies in accordance with an embodiment of the present invention.
Figure 2:
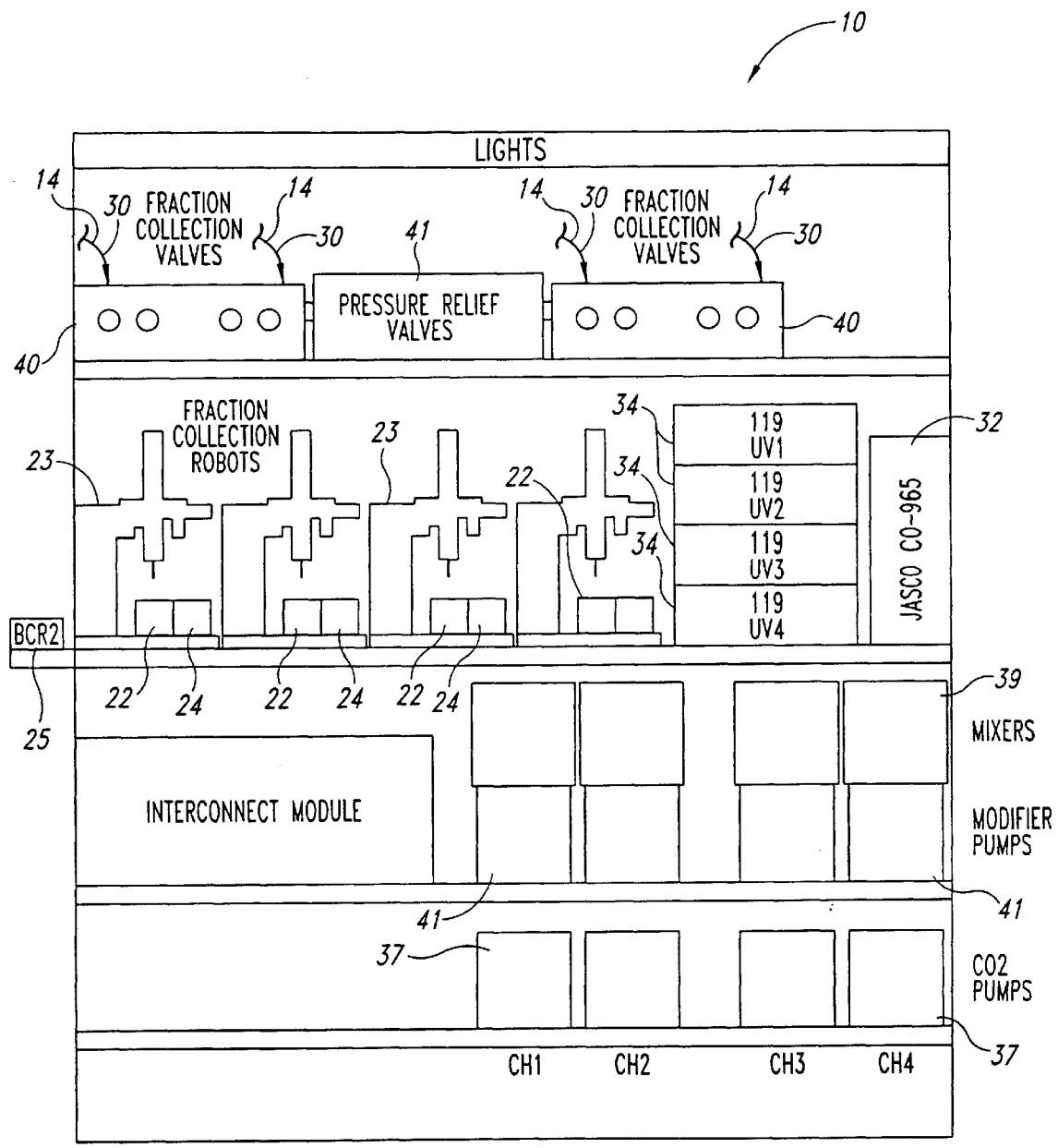
FIG. 2 is a schematic view of another portion of the multiple channel high throughput purification system of FIG. 1.
Figure 3A:
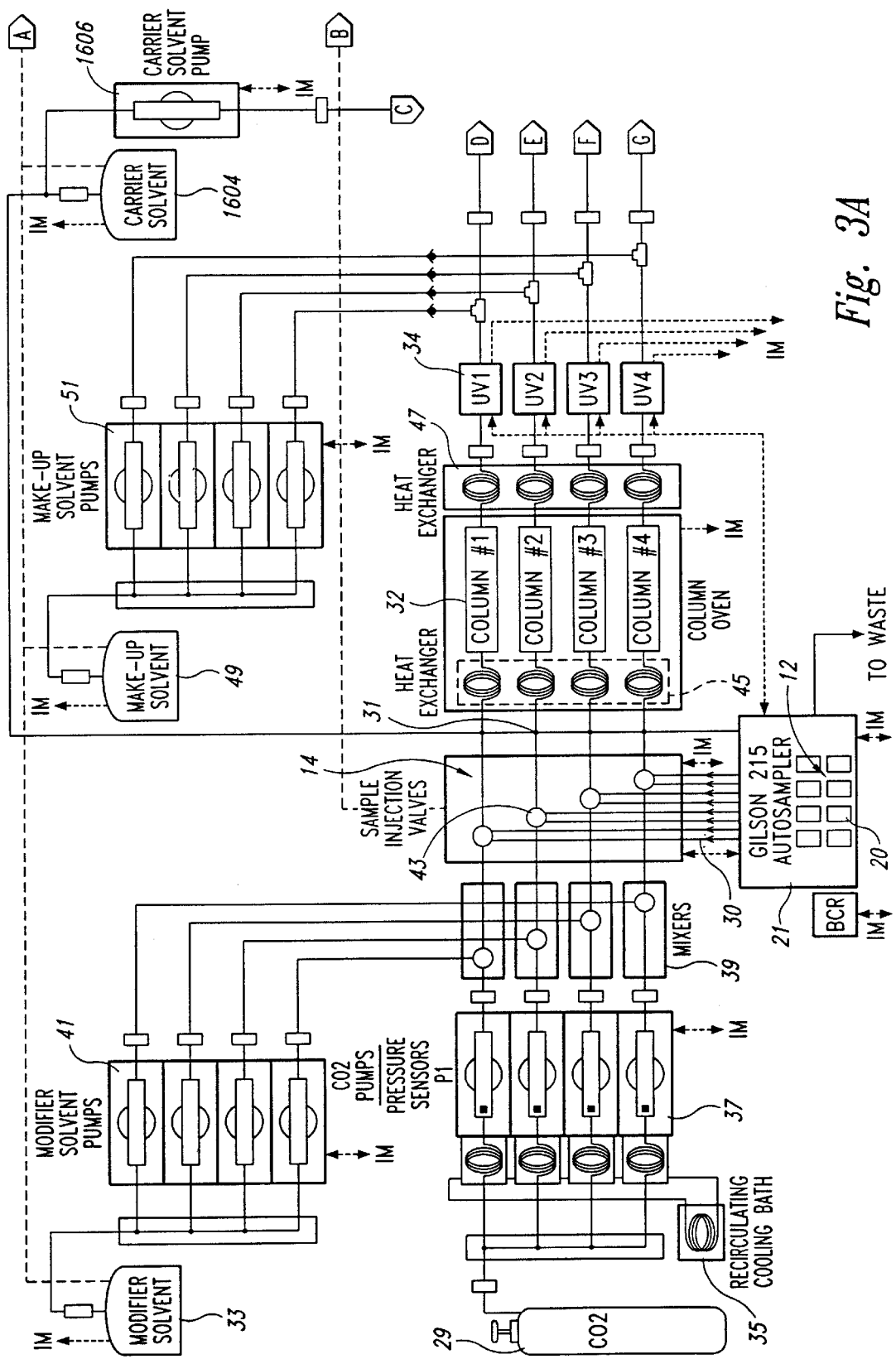
FIGS. 3A and 3B are schematic views of the multiple channel high throughput purification system of FIGS. 1 and 2, wherein the system has four channels.
Figure 3B:
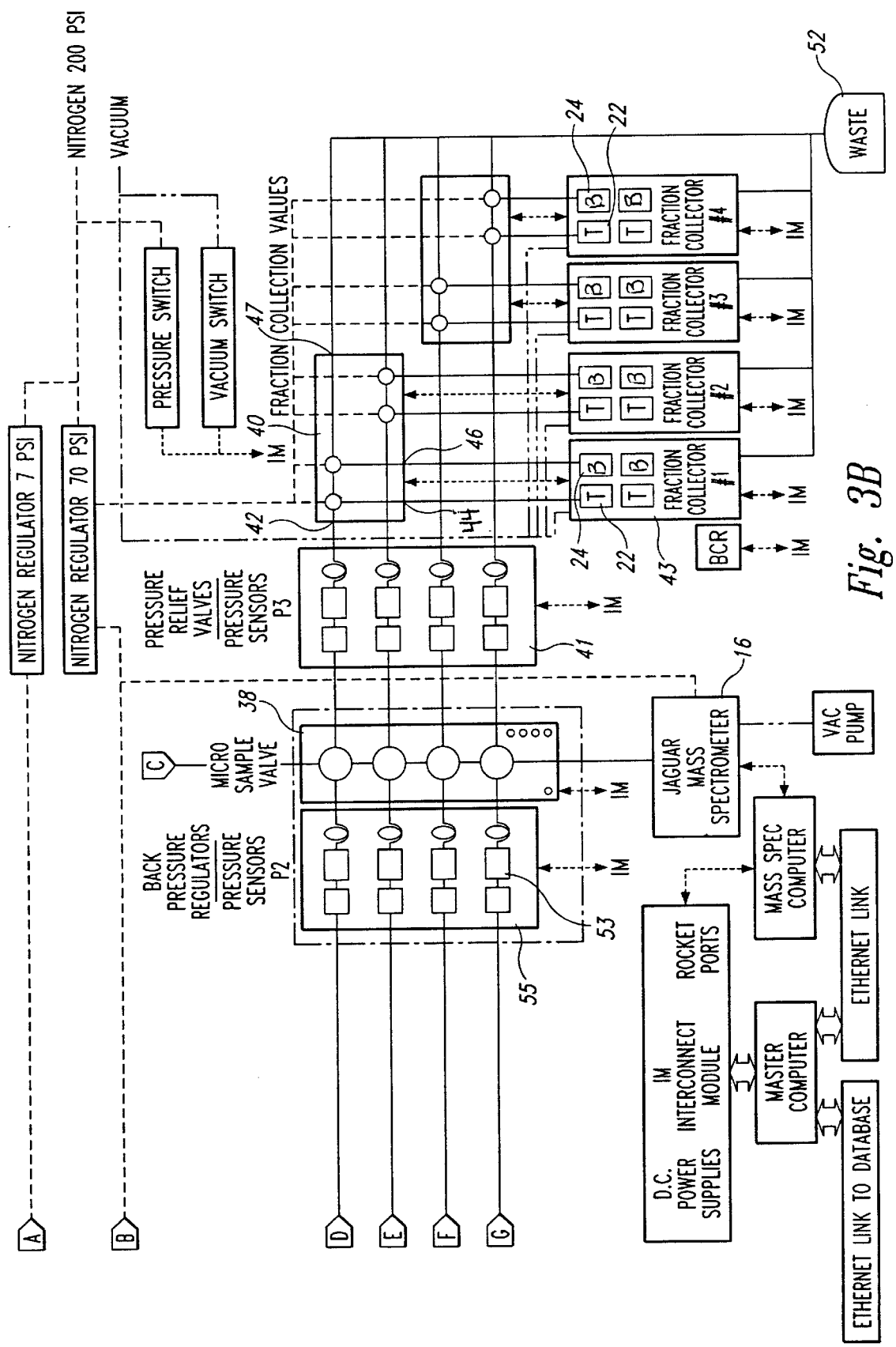

A multiple channel high throughput purification system 10 having a back pressure regulator assembly 55 and a pressure relief valve assembly in accordance with an illustrated embodiment is shown in FIGS. 1–3, and components of the system are shown in FIGS. 4–22. The illustrated purification system 10 is configured to simultaneously purify four samples 12 from a chemical library, wherein each sample is purified along a respective purification channel 14 in the system. Purification in the illustrated embodiment is achieved by chromatography, and more particularly by supercritical fluid chromatography (SFC), discussed in greater detail below.

Each channel 14 receives a selected sample from a supplying microtiter plate 20. Each channel 14 is coupled to a common analyzer, such as a mass spectrometer 16 that analyzes selected portions of the samples in accordance with a predetermined analysis priority protocol. In one embodiment, the analyzer includes a plurality of compound identification devices. In the illustrated embodiment, each supplying microtiter plate 20 includes a bar code or other selected symbology or tracking mechanism that provides information specific to that supplying microtiter plate. The purification system 10 includes a bar code reader 15 or the like that identifies the specific supplying microtiter plates 20 used for each purification run.

The components of each channel 14, including the mass spectrometer 16 and the bar code reader 15, are coupled to a computer controller 18 that monitors and controls operation of the components during a purification run. The mass spectrometer 16 is also connected to a computer 17 that can provide a user with additional control or monitoring capabilities during a purification run.

After each sample 12 is analyzed by the mass spectrometer 16, a substantially purified sample portion is distributed directly into a corresponding well of a receiving microtiter plate 22 (FIG. 2) or another selected sample collector. The other portions of the sample detected by the detector, known as reaction by-products, are distributed directly into a corresponding well in a second microtiter plate 24, also illustrated in FIG. 2. Accordingly, the four samples 12 are drawn from the supplying microtiter plate 20, purified, and each sample is deposited directly into a corresponding well location in two receiving microtiter plates 22 and 24, one containing the purified target compound and the other containing the reaction by-products. In one embodiment, the four samples are drawn from the supplying microtiter plate sequentially by the same drawing needle assembly. In an alternate embodiment, the four samples are drawn substantially simultaneously by a drawing assembly having four drawing needles.

The receiving microtiter plates 22 and 24 have bar codes or the like on them, and a bar code reader 25 (FIG. 2) is provided adjacent to the receiving microtiter plates. The second bar code reader 25 is also coupled to the computer controller 18 (FIG. 1) to identify and track the samples deposited into the selected wells of each microtiter plate. The purified target compounds in the microtiter plates 22 and 24 can then be screened in a selected manner in an effort to locate a specific target compound.

The microtiter plates 22 are securely retained in an automated fraction collection assembly 23 coupled to the computer controller 18 (FIG. 1). The fraction collection assembly 23 directs selected sample portions of either purified target components or purified reaction by-products to selected wells of the microtiter plates 22 or 24. The fraction collection assembly 23 is automated and configured to pick up, clean, disposable or reusable expansion chambers in which vaporous sample portions are condensed and then delivered to the microtiter plates 22 or 24. The fraction collection assembly 23 includes a wash station in which sample dispensing needles are washed after a sample portion is delivered to the respective microtiter plate and before the next set of clean expansion chambers are picked up for delivery of the next sample portions.

In the purification process of the illustrated embodiment, selected supplying microtiter plates 20 are identified by the bar code reader 15 and positioned on an autosampler 21 (FIG. 1). In one embodiment, the autosampler 21 is a Gilson 215 autosampler, manufactured by Gilson, Inc. of Middleton, Wis. As best seen in the schematic diagram of FIG. 3, each sample is drawn by the autosampler 21 from a selected well of a supplying microtiter plate 20 and is fed into a sample flow path 30 of a respective one of the four channels 14. The four samples 12 are substantially simultaneously introduced into the respective purification channels 14. Although the illustrated embodiment substantially simultaneously purifies four samples 12, other numbers of samples can be simultaneously purified with a system in accordance with the present invention.

As best seen in FIG. 3, the sample 12 is combined with carbon dioxide from a $CO_2$ source 29 and a modifier solvent from a solvent source 33 to form a carrier flow that flows through the respective channel 14 at a selected flow rate. The carbon dioxide flows through a heat exchanger 36 is chilled with a recalculating cooling bath 35 and is pumped via a $CO_2$ pump 37 to a mixer 39. The flow of $CO_2$ is also passed through a pulse damper to minimize any pulsation caused by the pump 37. The modifier solvent flows through a solvent pump 41 into the mixer 39 where the solvent is mixed with the carbon dioxide. The carbon dioxide and solvent mixture then flows to a sample injection valve 43, where the sample 12 is received from the autosampler 21 and is combined with the carrier flow to form the sample flow 31.

The sample flow 31 is passed through a heat exchanger 45 at which time the fluid becomes supercritical, and then a separation media, such as an SFC column 32, that spatially separates the sample components within the sample flow 31. Accordingly, each sample component is spaced apart from the other components and separated in time as the sample flow exits the SFC column 32 and moves through the purification channel 14.

Figure 4:
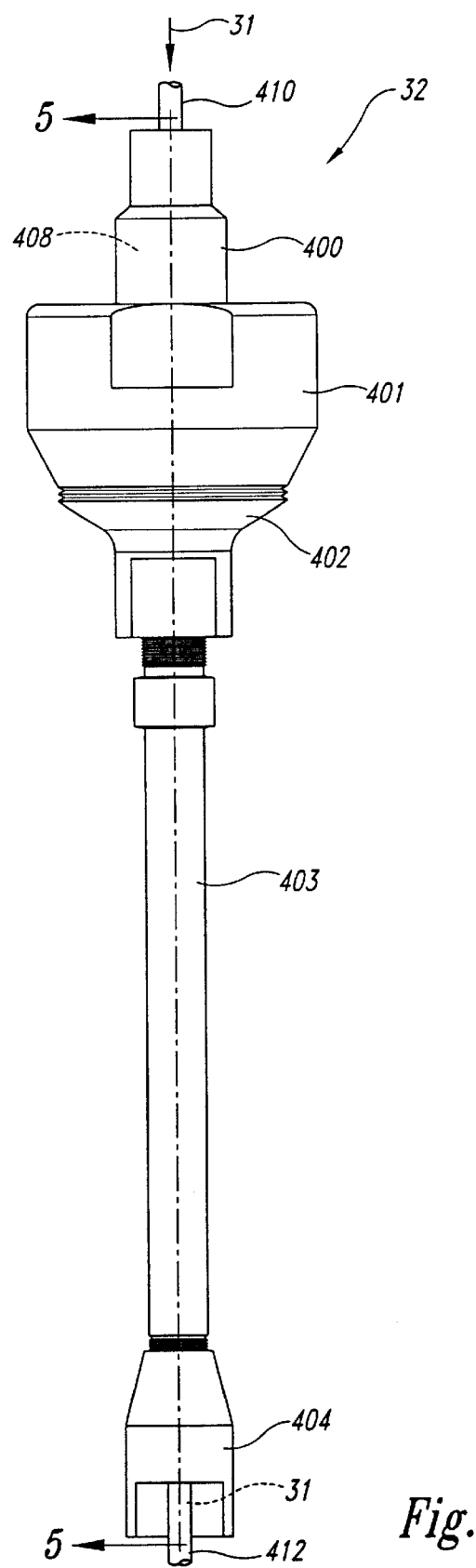
FIG. 4 shows a side elevation view of a two-piece column of the purification System of FIG. 3.
Figure 5:
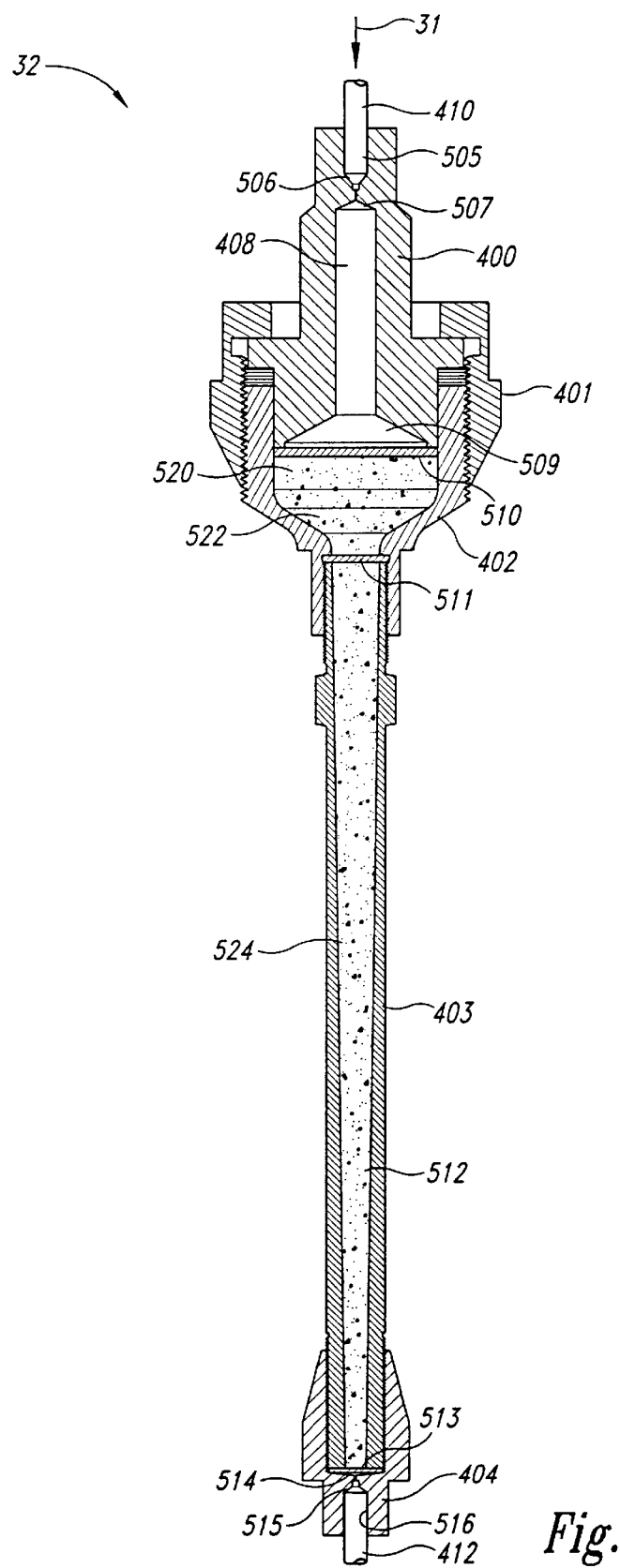
FIG. 5 shows a cross-sectional view of the two-piece column taken substantially along line 5—5 of FIG. 4.

In one embodiment of the invention, the column 32 is a two-piece column, as illustrated in FIGS. 4 and 5, for use in supercritical fluid chromatography. As best seen in FIG. 4, the components of the column 32 include an upper dilution body 400 that defines that a dilution chamber 408 therein. The top portion of the dilution body 400 is connected to an inlet tube 410 through which the sample flow 31 passes and moves into the column 32. The upper dilution body 400 is connected to a loading body 402 and securely retained in place by a top end cap 401. The dilution chamber body 400 is compressed downwardly by the top end cap 401 that screws externally onto the threads of the loading body 402. In an alternate embodiment for use in liquid chromatography, the dilution chamber is not needed, so the column 32 does not include the dilution body attached to the loading body.

The dilution chamber body 400, the top end cap 401, and the loading body 402 of the illustrated embodiment are made from an inert material, such as stainless steel. In alternate embodiments, other inert materials can be used for construction of the column's components. A separation body 403 at its upper end is attached to the lower portion of the loading body 402. The lower end of the separation body 403 is securely connected to a bottom end cap 404 that connects to an outlet tube 412, through which the separated sample flow 31 exits the column 32.

As best seen in a cross-sectional view of FIG. 5, the sample flow 31 enters the column 32 at a top-threaded port 505 to which an inlet tube 410 is sealed by an external ferrule that seats onto the top ferrule sealing point 506 in the threaded port. The sample flow is directed radially from the inlet tube 410 into the upper dilution chamber 408 by means of an inverted top funnel portion 507. The top funnel portion 507 is substantially conical in geometry and it defines the top of the dilution chamber 408. The main body of the dilution chamber 408 is substantially cylindrical, although it can be constructed with other geometric shapes in alternate embodiments. The bottom of the dilution chamber 408 has an inverted bottom funnel portion 509 that flares radially outwardly from the dilution chamber's main body. Accordingly, the bottom funnel portion 509 flares to a lower opening having a greater diameter than the dilution chamber's main body. The lower opening of the bottom funnel portion 509 is positioned over a top frit 510 located below the dilution chamber 408.

The dilution chamber's entire volume is void of stationary phase material. Dilution of the sample in the sample flow takes place in the dilution chamber 408 as the sample flow moves downwardly through the main body to the bottom funnel portion 509, where the sample flow passes through the top frit 510. The top frit 510 distributes the sample over a column bed 512 in a loading region 520 directly below the top frit 510. Sealing of the dilution chamber 408 is achieved at the top frit 510 where the dilution chamber body 400 fits internally into the loading body 402.

The loading body 402 has a loading region 520 below the top frit 510 and a transition region 522 below the loading region. The loading and transition regions 520 and 522 in the loading body 402 are filled with a stationary phase material, such as cyano, that defines a column bed 512 in the column 32. In alternate embodiments, other stationary phase materials can be used to form the column bed 512. The loading region 520 has an inner diameter approximately two or more times greater than the inner diameter of the separation region 524, and a length of approximately one-half or less than the length of the separation region. In the loading region 520, the sample flow traverses downwardly through the column bed 512 into the transition region 522, which has a conical shape as defined by the loading body 402. The transition region 522 directs the sample flow into the separation region 524 of the column bed 512.

The top of the separation body 403 is threadably attached to the bottom of the loading body 402 by a threaded connection and is sealed by an adjoining frit 511 sandwiched therebetween. The separation body 403 of the illustrated embodiment is made of stainless steel and is shaped so the interior chamber containing the separation region 524 of the column bed 512 has a tapered cylindrical geometry with a wider upper end and a narrower lower end. The interior chamber of separation region 524 of the column bed 512 is filled with the stationary phase material. The sample flow travels downwardly through the column bed 512 in the separation region 524 past a bottom frit 513 and onto a bottom fluid funnel 514 formed in the bottom end cap 404. The bottom of the separation region 524 is sealed by the bottom end cap 404 screwed externally onto the separation body 403. The bottom frit 513 is sandwiched between the bottom end cap 404 and the separation body 403. The bottom fluid funnel 514 is conical and directs the fluid into a bottom threaded port 516 formed in the bottom end cap 404 to which the outlet tube 412 can be screwed. The outlet tube 412, when screwed into the outlet port 516, is sealed against the bottom end cap 404 at a bottom ferrule sealing point 515 by use of an external ferrule.

Figure 6:
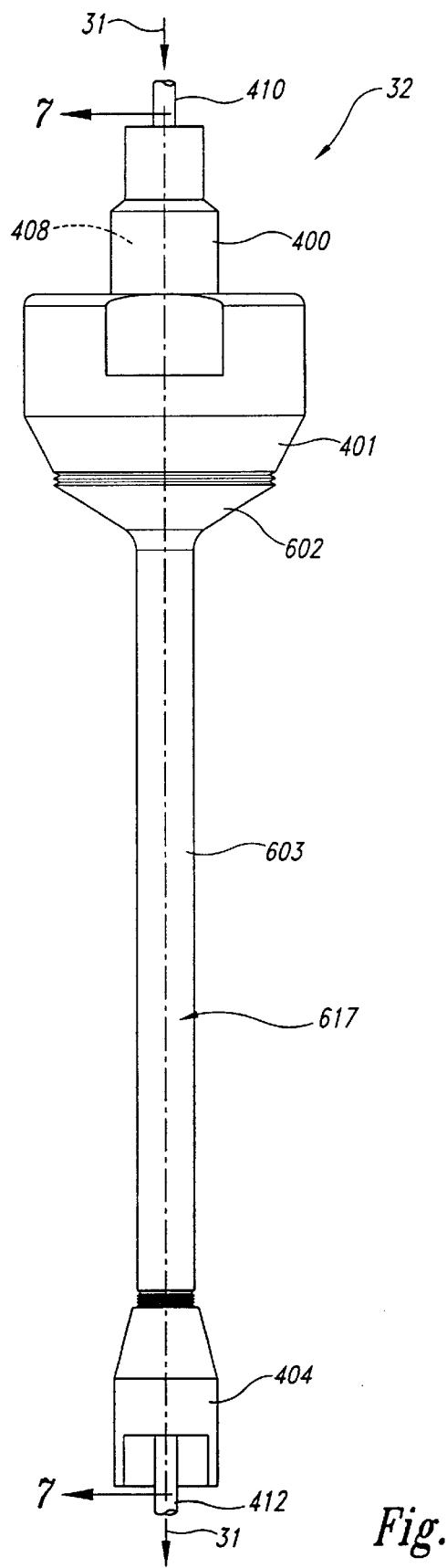
FIG. 6 shows a side elevation view of an alternate one-piece column usable in the purification system.

In an alternate embodiment illustrated in FIG. 6, the column 32 is a "one-piece" column. In view of the similarities between the two embodiments, components that are the same between the two embodiments are identified in the figures by the same reference numbers for purposes of clarity. The one-piece column is substantially the same as the two-piece column discussed above, with the exception that the loading body 602 and the separation body 603 are integrally formed from a single stainless steel unit to define a One-Piece Loading and Separation (OPLAS) body 617. Accordingly, the upper frit 511 used in the two-piece column is not needed and thus omitted.

Figure 7:
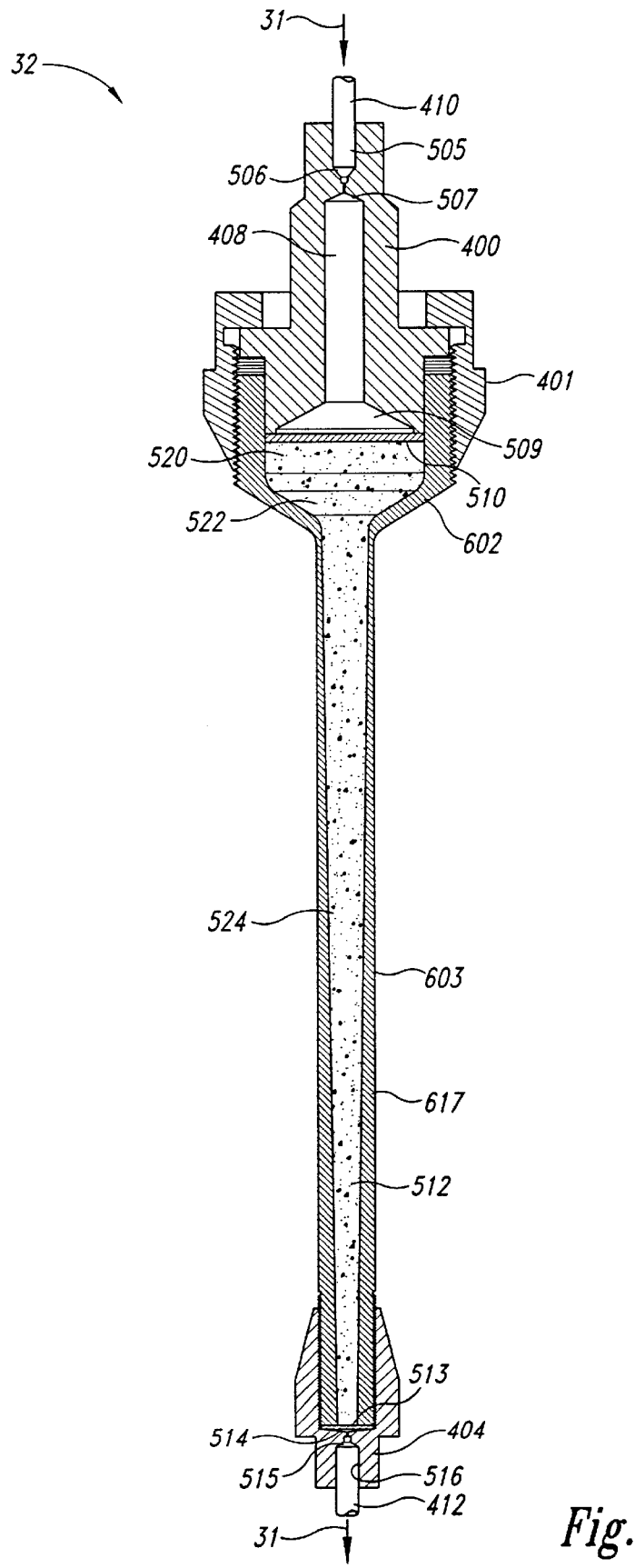
FIG. 7 shows a cross-sectional view of the one-piece column taken substantially along line 7—7 of FIG. 6.

As best seen in the cross-sectional view of FIG. 7, the dilution chamber body 400 fits internally into the OPLAS body 617 and is secured by the top end cap 401 that screws externally onto the OPLAS body. The lower end of the OPLAS body 617 screws internally into the bottom end cap 404. Accordingly, the loading region 520 formed in the OPLAS body 517 has a diameter approximately two or more times greater than the inner diameter of the separation region 524, and a length of approximately one-half or less than the length of the separation region.

Figure 8A:
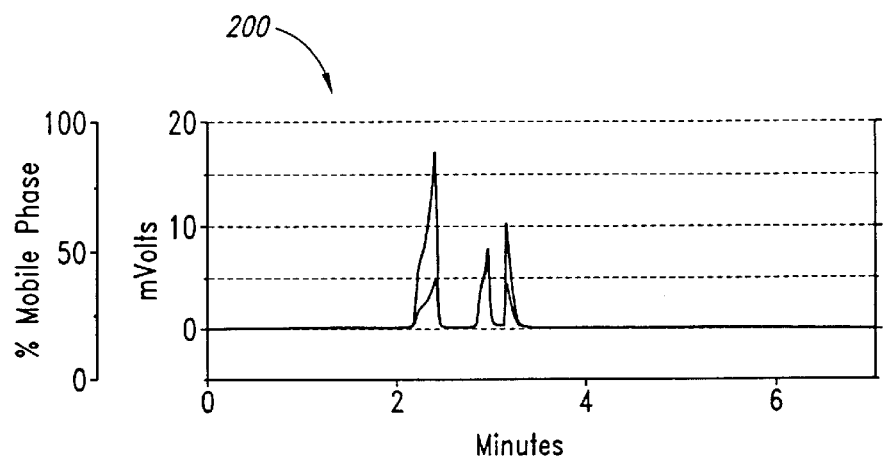
FIGS. 8A–C show results of three chromatographic runs showing the improvement over prior art.
Figure 8B:
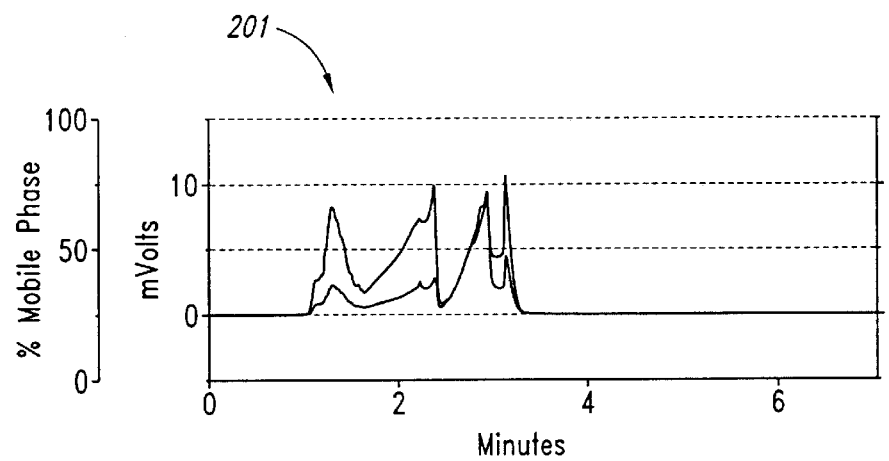
Figure 8C:
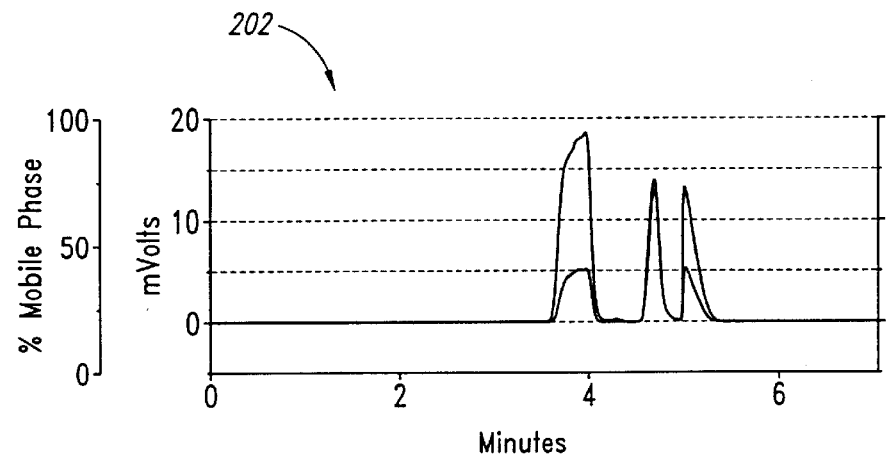

FIGS. 8A–C show graphical results from three chromotographic runs showing improvement over the prior art provided by the column 32 in accordance with the present invention. All three chromotographic runs were injected with the same mass loading of a three-compound mixture and run under the same chromotographic conditions. Run 200 (FIG. 8A) shows the separation results using a single prior art column injected with a small volume solvent mixture. Run 201 (FIG. 8B) shows the separation results using the same prior art single column as in run 200, wherein the prior art column was injected with a large volume solvent mixture. Run 202 (FIG. 8C) shows the separation results using a two-part column 32 in accordance with an embodiment of the present invention as discussed above. Run 202 was injected with the same large volume solvent mixture as run 201.

The first portions of the column 32 (e.g., the loading and transition portions) have a larger inner diameter than the column's second portion (the separation region) and a shorter length than the column's second portion. Accordingly, the column 32 in accordance with the present invention can handle large volume solvent mixtures with multiple compounds and provide highly accurate separation and detection of the different compounds, such as by use of a mass spectrometer or the like. This accuracy in conjunction with corresponding speed for handling large volume solvent mixtures with multiple compounds provides a faster and more efficient processing capability.

Referring again to FIG. 3, the sample flow 31 exits the SFC column 32, flows through another heat exchanger 47, and flows to a detector 34. The detector 34 is adapted to detect the different components or peaks in the sample flow 31 that have been separated from each other by the SFC column 32. In the illustrated embodiment, the detectors 34 are ultraviolet light (UV) detectors. While UV detectors are used in the illustrated embodiment, other detectors can be used, such as infrared (IR) detectors or any other suitable detector capable of identifying a peak within the sample flow 31.

Each detector 34 is coupled to the common computer controller 18. When the detector 34 identifies a peak, the detector provides a signal to the computer controller 18 indicating the peak. Because the sample flow rate is known in each channel 14, the computer controller 18 can calculate the location of each peak within each channel 14 as the sample flow 31 moves through the channel. As an example, when two peaks are detected in the same sample flow 31, the computer controller 18 calculates and monitors where those peaks are within the channel 14. The computer controller 18 also calculates where the peaks are relative to each other during the entire purification process.

As the sample flow 31 moves through the purification channel, it is in a vaporous state. After the sample flow 31 exits the detector 34, additional solvent, referred to as makeup solvent 49, is added to the sample flow as needed to increase the volume of liquid in the sample flow to facilitate transport of the sample to the fraction collector assembly (discussed below). The makeup solvent 49 is pumped from a solvent container by solvent pumps 51 into the respective purification channel 14. The solvent container and the solvent pumps 51 are each coupled to the computer controller 18 so the computer controller can monitor the solvent volumes used and can control the solvent pumps as necessary for the selected purification run. The computer controller 18 also monitors the amount of makeup solvent 49 needed within the purification channel during a run, so it can detect if a potential problem arises, and can provide an alarm or other warning to an operator of the system.

After any of the makeup solvent 49 is added to the sample flow 31, the sample flow passes through a back pressure regulator module 53 in a back pressure regulator assembly 55. The back pressure regulator module 53 detects and controls the back pressure within the channel 14 to maintain the desired pressure within the channel.

Figure 9:
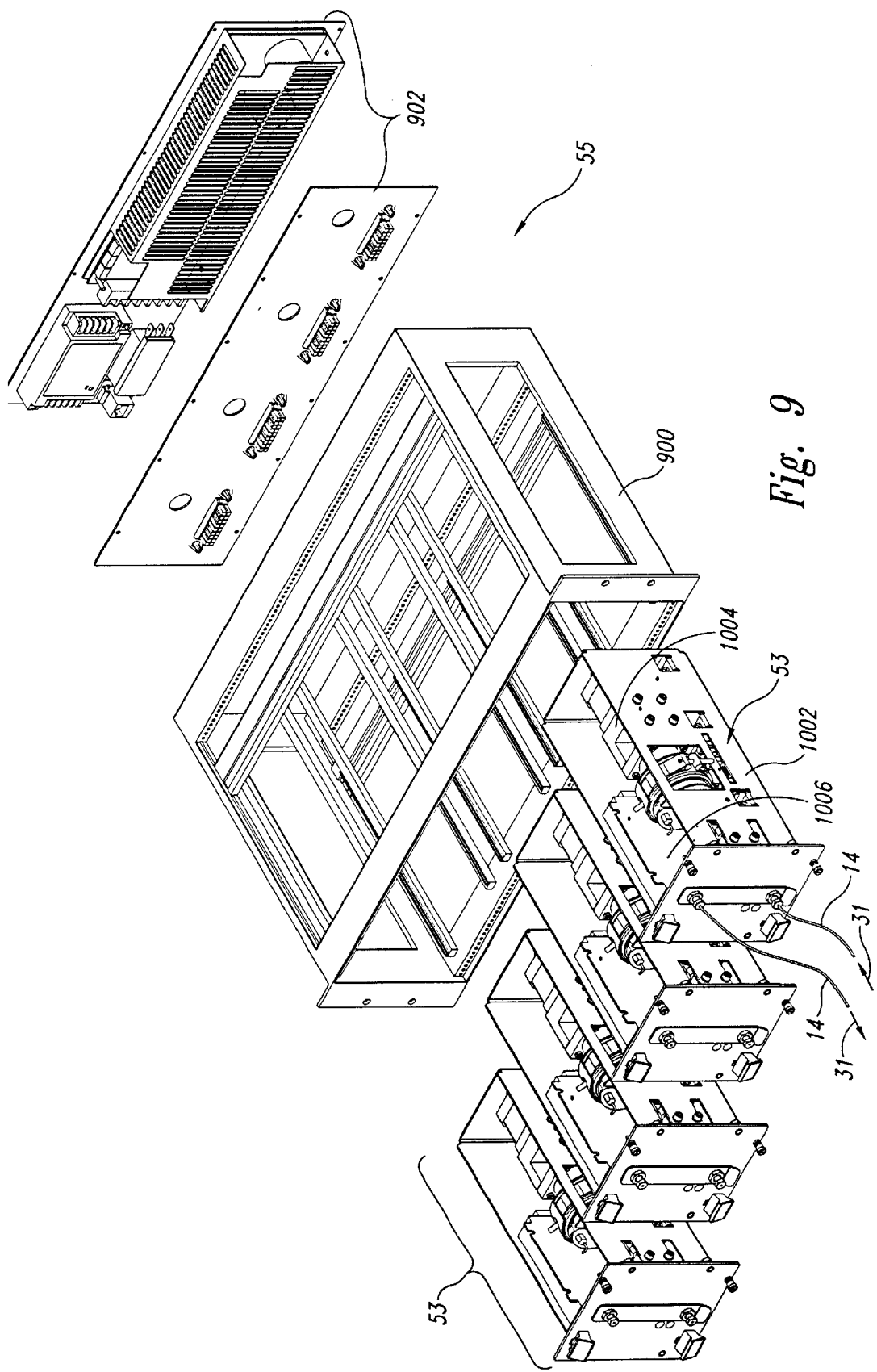
FIG. 9 is an enlarged exploded isometric view of a back pressure regulator assembly from the purification system of FIG. 3.

As best seen in FIG. 9, the back pressure regulator assembly 55 includes a housing 900 that removably retains four back pressure regulator modules 53, one for each purification channel 14. The assembly 55 also includes a communication panel 902 to which the back pressure regulator modules 53 attach for communication to and from the computer controller 18 (FIG. 3). The modules 53 plug into the housing 900 and onto the communication panel 902. Accordingly, if a new or substitute module 53 is needed in the purification system, it can be installed quickly and easily upon unplugging one module and plugging in the replacement module.

Figure 10:
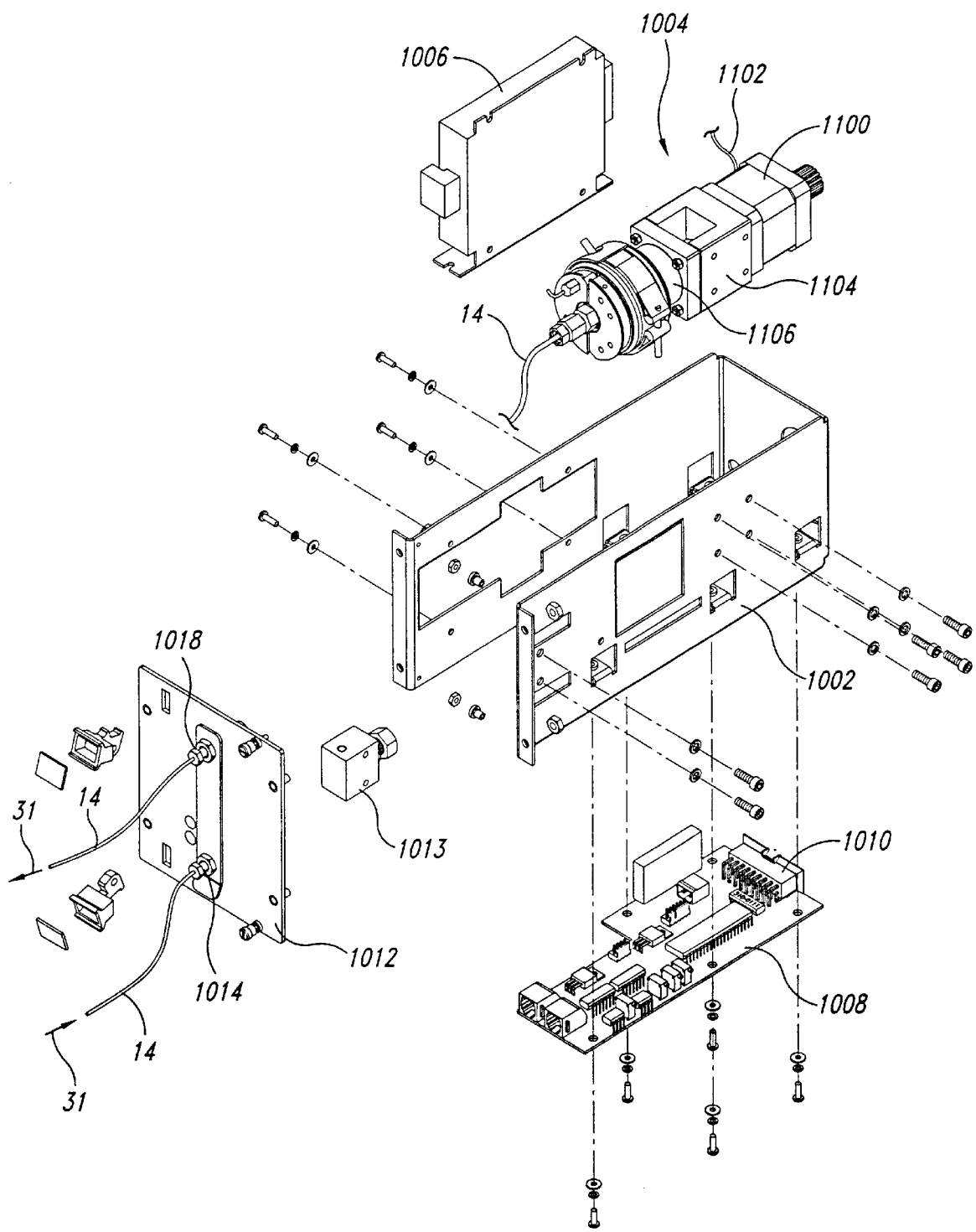
FIG. 10 is an enlarged exploded isometric view of a back pressure regulator module from the assembly of FIG. 9.

As best seen in FIG. 10, the pressure regulator module 53 includes a housing 1002 that contains and protects a regulator assembly 1004. The regulator assembly 1004 controls the back pressure in the sample flow as it moves through the respective purification channel 14. The regulator assembly 1004 is electrically connected to a stepper motor controller 1006 which activates and adjusts the regulator assembly as needed during a purification run. The stepper motor controller 1006 is connected to a printed circuit board 1008 which also attaches to the housing 1002. The printed circuit board 1008 includes a plurality of connectors 1010 that releasably plug into the communication panel 902 (FIG. 9) of the regulator assembly. Accordingly, communication to and from the computer controller 18 is provided to the pressure regulator module 53 through the printed circuit board and to the regulator assembly 1004 via the stepper motor controller 1006.

The pressure regulator module 53 also includes a front faceplate 1012 that mounts to the housing 1002. The front faceplate 1012 has an inlet port 1014 into which the tubing of the purification channel extends so as to allow the sample flow 31 to pass into the pressure regulator module 53. The sample flow passes through a pressure sensor 1013, which is also coupled to the printed circuit board 1008, so as to identify the sample flow's pressure. After the sample flow 31 enters the regulator assembly 1004 and the sample flow's pressure is modified as needed, as discussed in greater detail below, the sample flow exits the pressure regulator module 53 through an outlet port 1018 on the front faceplate 1012.

Figure 11:
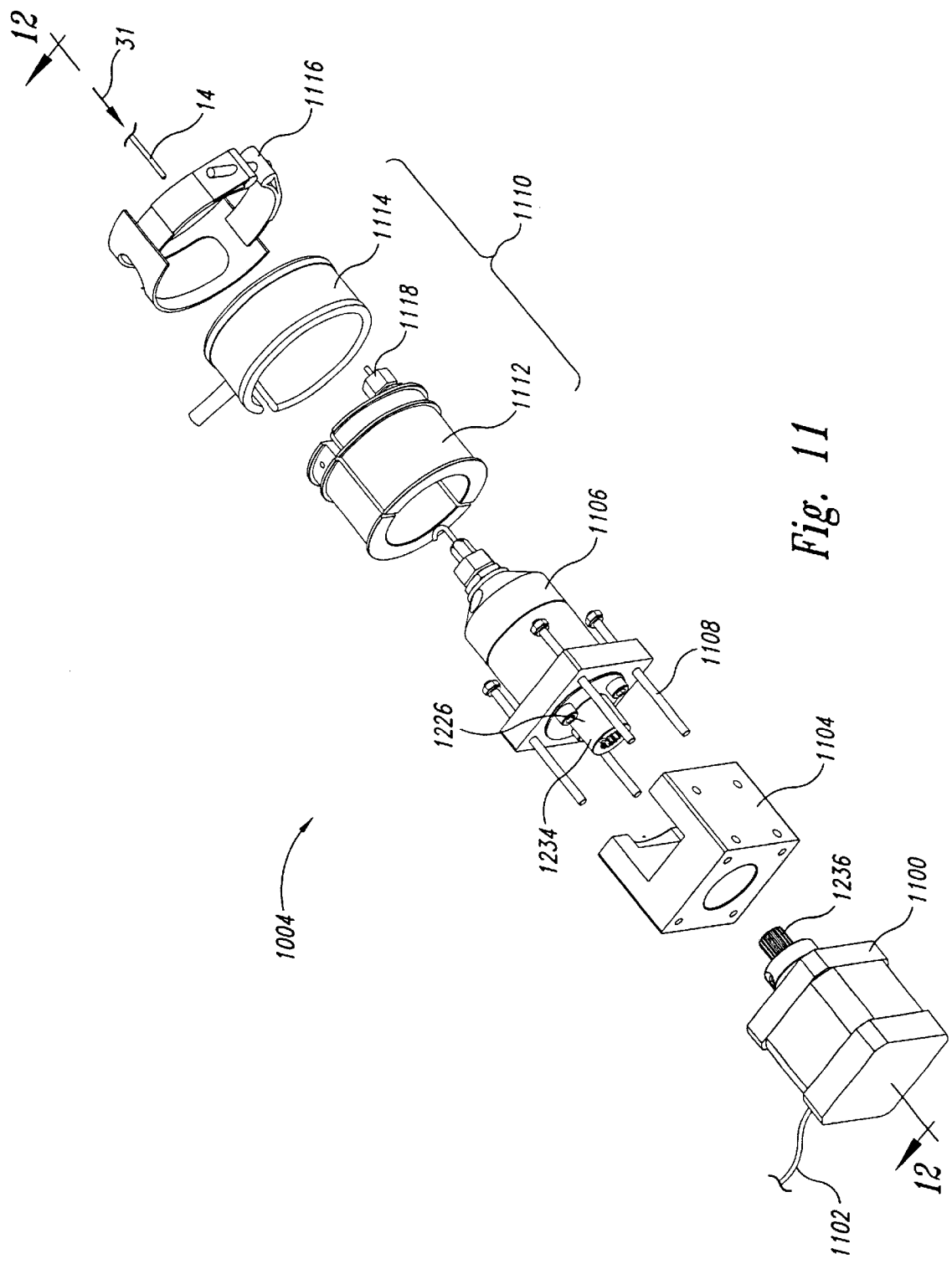
FIG. 11 is an enlarged isometric view of a regulator/motor assembly of the back pressure regulator module of FIG. 10.

As best seen in FIGS. 11 and 12, the regulator assembly 1004 includes a stepper motor 1100 having wiring 1102 that connects to the stepper motor controller 1006 (FIG. 10). The stepper motor 1100 is connected to a motor mount 1104 that interconnects the stepper motor to a back pressure regulator 1106. The back pressure regulator 1106 is securely retained to the stepper motor 1100 by a plurality of mounting screws 1108 that extend through the motor mount 1104 and screw into the housing of the stepper motor 1100.

The regulator assembly 1004 also includes a heater 1110 adapted to heat the sample flow 31 within the purification channel's tubing so as to prevent formation of ice crystals or the like that may occur as a result of pressure differentials occurring across the pressure regulator. The heater 1110 includes a heat transfer body 1112 that extends over the back pressure regulator 1106 and a heater band 1114 clamped onto the heat transfer body by a band clamp 1116. The heater band 1114 is coupled to the computer controller 18 to allow the heater band to regulate its temperature to provide different heating configurations to the back pressure regulator during a purification run. The heat transfer body 1112 includes a temperature sensor 1118 that monitors the temperature of the heat transfer body during the purification run. The temperature sensor 1118 is coupled to the computer controller 18 (FIG. 3) so the computer controller can regulate the heat provided from the heater band 1114 as needed during operation of the regulator assembly 1004. The heater 1110 is controlled to prevent formation of ice or crystals in the pressure regulator 1106.

Figure 12A:
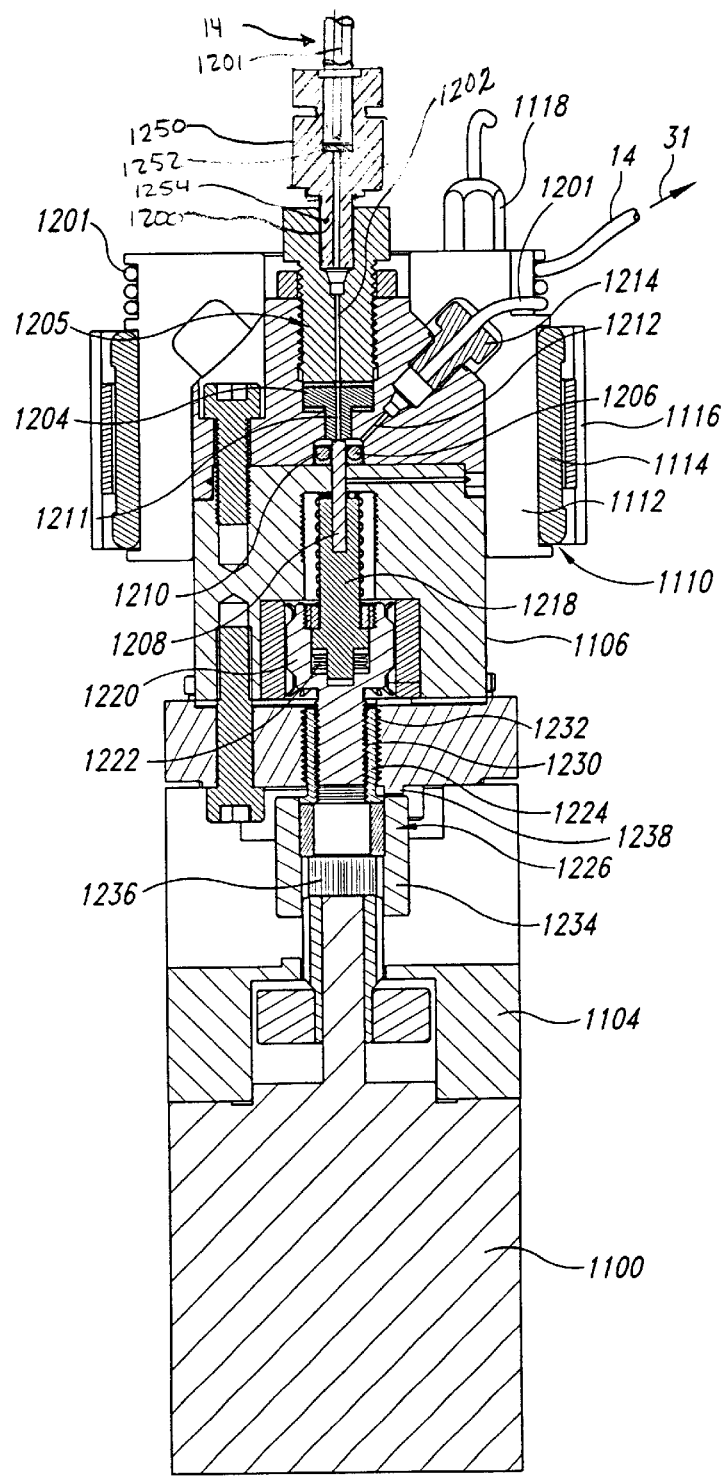
FIG. 12A is an enlarged cross-sectional view of the regulator assembly taken substantially along line 12—12 of FIG. 11.

As best seen in FIG. 12A, the regulator 1106 has a flow filter 1250 that receives the purification tube 1201 carrying the sample flow 31. The flow filter 1250 includes a frit 1252 or other filtering member positioned in the path of sample flow 31. The sample flow 31 passes through the frit 1252, and the frit filters out any particulates in the sample flow before the flow progresses through the regulator 1106. The flow filter 1250 has a connector end 1254 that extends into and is securely received by an inlet port 1200 that receives the filtered sample flow 31. In an alternate embodiment, the flow filter 1250 is not used, so the purification tube entering the regulator 1106 extends directly into the inlet port 1200.

The inlet port 1200 has an inlet channel 1202 that communicates with a nozzle 1204 positioned below the inlet port. The nozzle 1204 in the illustrated embodiment is a ceramic component having a diamond coating so as to provide an extremely hard, erosion-resistant, and durable nozzle within the regulator. The nozzle 1204 is exposed to very harsh conditions, including caustic solvents and pressures of approximately 2000 psi or greater. The inlet port 1200 is threadably connected to the nozzle retainer 1205 so the inlet port is easily removable to provide access to the nozzle 1204 if replacement of a nozzle is necessary.

The nozzle 1204 includes an inlet channel 1211 extending therethrough that communicates with a very small chamber that receives the sample flow 31 from the nozzle's inlet channel. The lower end of the inlet channel 1211 forms a nozzle orifice through which the sample flow passes. A stem 1208 positioned below the nozzle 1204 extends through a seal 1210, into the small chamber 1206, and terminates immediately adjacent to the nozzle orifice at the lower end of the inlet channel 1211. The stem 1208 is moveable relative to the nozzle orifice so as to adjustably close the flow path through the regulator 1206. In the illustrated embodiment, the stem 1208 is a sapphire stem. In alternate embodiments, the stem 1208 can be made of other very hard, erosion-resistant, materials, such as diamond, ruby or the like. The stem 1208 is moveable relative to the nozzle 1204 to adjust the opening size so as to regulate the pressure of the sample flow 31.

Figure 12B:
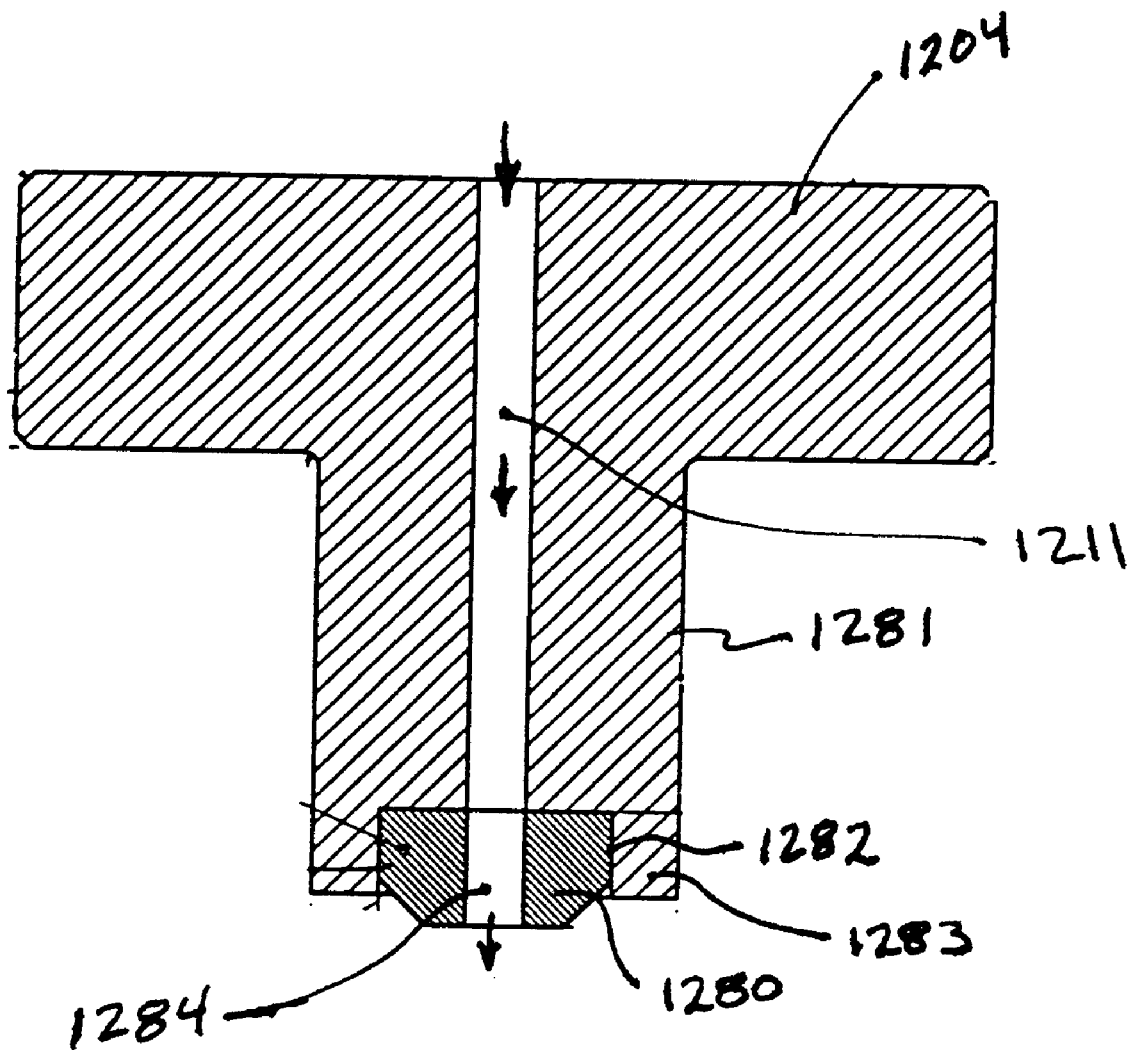
FIG. 12B is an enlarged cross-sectional view of an alternate nozzle in the regulator assembly of FIG. 12A in accordance with an alternate embodiment.

As best seen in FIG. 12B, the nozzle 1204 in an alternate embodiment has a nozzle body 1281 and a nozzle insert 1280 retained in a cavity 1282 formed in the nozzle body's lower end 1283 facing the stem 1208 (FIG. 12A). The nozzle insert 1280 of the illustrated embodiment is retained in the cavity by a rolled crimp formed in the lower end of the nozzle body 1281. The nozzle insert 1280 in another embodiment can be retained in other suitable ways to securely hold the insert in place in the nozzle's cavity.

The nozzle insert 1280 is made of a very hard, erosion-resistant material such as sapphire, ruby, diamond or other suitable material that exhibits sufficient hardness and erosion resistance. In one embodiment, the nozzle body 1281 is made of a ceramic component, and the nozzle insert 1280 is sapphire. The nozzle insert has an aperture 1284 aligned with the inlet channel 1211 in the nozzle body. The lower end of the aperture 1284 forms the nozzle orifice through which the sample flow passes.

The sample flow 31 moves from the nozzle 1204 through the orifice and into an outlet channel 1212 that is in fluid communication with the small chamber 1206. The outlet channel 1212 extends through an outlet port 1214 that receives the exit tube 1201 therein so as to carry the sample flow 31 out of the regulator 1106. The exit tube 1201 extends from the outlet port 1214 and wraps around the heat transfer body 1112 approximately two times so the exit tube is heated, thereby preventing the formation of ice crystals within the purification tube and condensation on the outside of the exit tube. The purification tube 1201 then extends from the heat transfer body 1112 away from the regulator assembly and to the outlet port 1018 on the regulator module's faceplate 1012 (FIG. 10) as discussed above.

In the illustrated embodiment, the stem 1208 is a sapphire stem having hardness and erosion-resistance characteristics suitable for use in the high pressure and harsh environment within the regulator assembly 1004. The sapphire stem 1208 is connected at its lower end to a rod 1218 movably positioned within a holding member 1220 having a threaded lower end. The holding member 1220 contains a biasing member 1222, such as Bellville washers, wave washers, or the like, that bias the rod 1218 and the stem 1208 toward the nozzle 1204. When the stem 1208 directly engages the nozzle 1204 and additional force is exerted on the stem, the biasing member 1222 will be compressed so as to avoid damaging the sapphire stem 1208 or the nozzle 1204 during operation. The biasing member 1222, however, has a sufficient spring stiffness so it is not compressed during normal pressures of the sample flow within the tubing of the purification channel 14 during a purification run.

Adjustment of the regulator assembly 1106 is provided by dual concentric screws that move the stem 1208 relative to the nozzle 1204. As best seen in FIG. 12, the holding member 1220 is threaded into internal threads 1230 formed in a shaft 1224 of an adjustment screw 1226. In the illustrated embodiment, the internal threads 1230 have a pitch of 28 threads per inch (tpi). The adjustment screw's shaft 1224 also has external threads 1232 that screw into a threaded aperture in the regulator body 1106. In the illustrated embodiment, the external threads 1232 have a pitch of 27 tpi. Accordingly, the external threads 1232 of the adjustment screw 1226 have a thread pitch different than the pitch value of the internal threads 1230. The internal and external threads 1230 and 1232 are both right-handed pitch threads oriented in opposing directions so as to form the dual concentric adjustment screw configuration for attenuated movement of the stem 1208 relative to the nozzle 1204 for each turn of the adjustment screw.

The adjustment screw 1226 has an internal driving spline 1234 that securely engages a drive spline 1236 on the stepper motor 1100. The drive spline 1236 is press fit into the internal driving spline 1234. When the stepper motor 1100 is activated by the computer controller 18 (not shown), the driving spline 1236 rotates, thereby rotating the adjustment screw 1226. As the adjustment screw 1226 rotates one revolution, the dual concentric screw configuration counteracts the range of motion of the holding member 1228, and thus the stem 1208. As an example, if the stepper motor 1100 rotates the adjustment screw one full revolution, the holding member 1220 moves only one pitch value because of the pitch differentiation between the internal and external threads 1230 and 1232.

In one embodiment, one revolution of the adjustment screw along the external threads 1232 would move the adjustment screw 1226 and the holding member 1220 approximately 0.0373 inches. The internal threads 1230, however, move in the opposite direction approximately 0.03571 inches, resulting in a net movement of approximately 0.0013 inches. Accordingly, the dual concentric screw configuration within the regulator 1106 provides for extremely accurate and fine adjustments of the stem 1208 relative to the nozzle 1204 to closely control pressure regulation within the sample flow 31 as it passes through the back pressure regulator assembly 1004.

The back pressure regulator 1004 is formed with a minimum amount of dead volume and unswept volume within the purification channel extending therethrough to prevent or minimize the risk of cross-contamination between purification runs for different samples. The back pressure regulator assembly is constructed with extremely durable components that will withstand the harsh environments experienced during the purification run at very high pressures, while providing sufficient safety characteristics to avoid damaging the back pressure regulator in the event of pressure spikes or the like.

In one embodiment, the stepper motor includes a rotational stop 1238 that prevents travel of the drive spline 1236 and, thus, rotation of the adjustment screw 1226 past a selected position relative to the regulator. The travel stop 1238 is positioned to block the stepper motor from driving the adjustment screw 1226 too far after the stem 1208 has engaged the nozzle 1204 thereby preventing the dual concentric threads from binding as a result of overdriving by the stepper motor.

The illustrated embodiment of the purification system utilizes the regulator assembly with the dual concentric screw configuration controlled by the computer controller 18. In alternate embodiments, the pressure regulator assembly 53 can be a stand alone regulator with selected control mechanisms.

As best seen in FIG. 3, the sample flow 31 travels from the pressure regulator assembly 55 to the microsample valve 38. The microsample valve 38 is operatively connected to the computer controller 18 and is activated by the computer controller when a peak in the sample flow 31 is moving past the microsample valve. Upon activation, the microsample valve 38 diverts a sampling from the sample flow 31 and directs it to the mass spectrometer 16 for analysis. The remaining portion of the sample flow 31 continues along the flow path of the respective channel 14 substantially uninterrupted. Each microsample valve 38 is activated so the sampling contains a selected portion of just the peak. The mass spectrometer 16 analyzes the sampling and determines whether the peak is a target compound or not.

As the four sample flows 31 moves simultaneously through the respective channels 14 and through the detectors 34, the peaks from the four channels will likely occur at separate times during the sample runs. Accordingly, the mass spectrometer 16 usually receives the samplings from the four channels with some time between the samplings. In some cases, however, two or more detectors 34 may detect a peak in its sample flow at the same time or at overlapping times during the sample run. The computer controller 18 is programmed with an analysis priority protocol that controls the activation sequence of the microsample valve 38 when peaks in the different channels 14 occur at the same time or overlapping times. Accordingly, the priority protocol controls the timing of when the samplings of the peaks are diverted to the mass spectrometer 16, so each peak can be analyzed separately by the same analyzer. In one embodiment, when a peak from separate channels 14 are detected simultaneously, the computer controller 18 activates the microsample valves 38 at different times so samplings of the respective peaks are sequentially directed to the mass spectrometer 16. Activation of each microsample valve 38 can be controlled by revising the computer controller's analysis priority protocol to provide sequential sampling.

Figure 13:
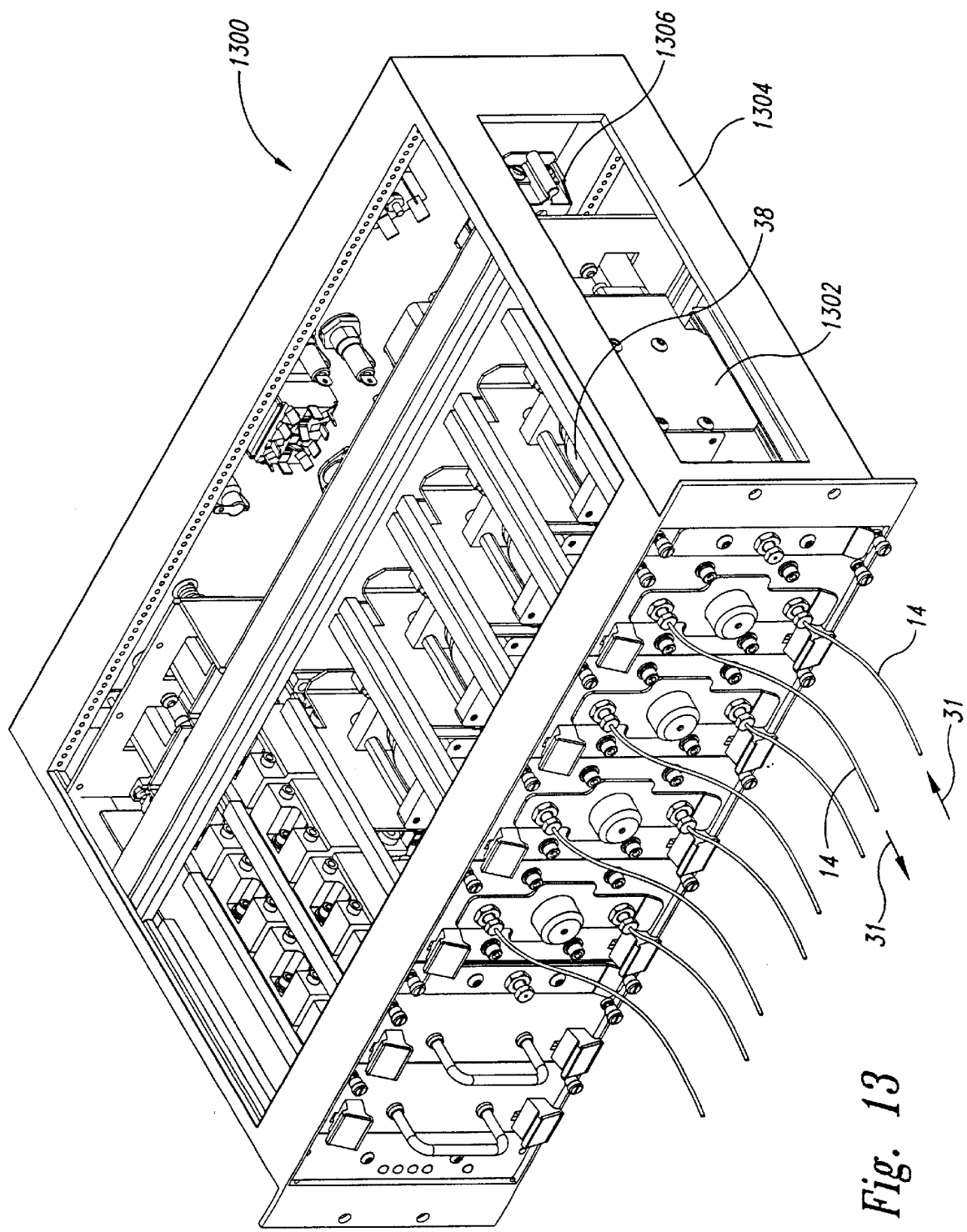
FIG. 13 is an enlarged isometric view of a microsample valve assembly from he purification system of FIG. 3.

As best seen in FIG. 13, the four microsample valves 38 are part of a microsample valve assembly 1300 that has four valve modules 1302. Each valve module 1302 contains a microsample valve 38 for its respective purification channel 14. The valve modules 1302 are removably received by a housing 1304 and plug into connectors coupled to a communication panel 1306. The communication panel 1306 is, in turn, coupled to the computer controller 18 (not shown), so the computer controller can control the activation of each microsample valve 38.

Figure 14A:
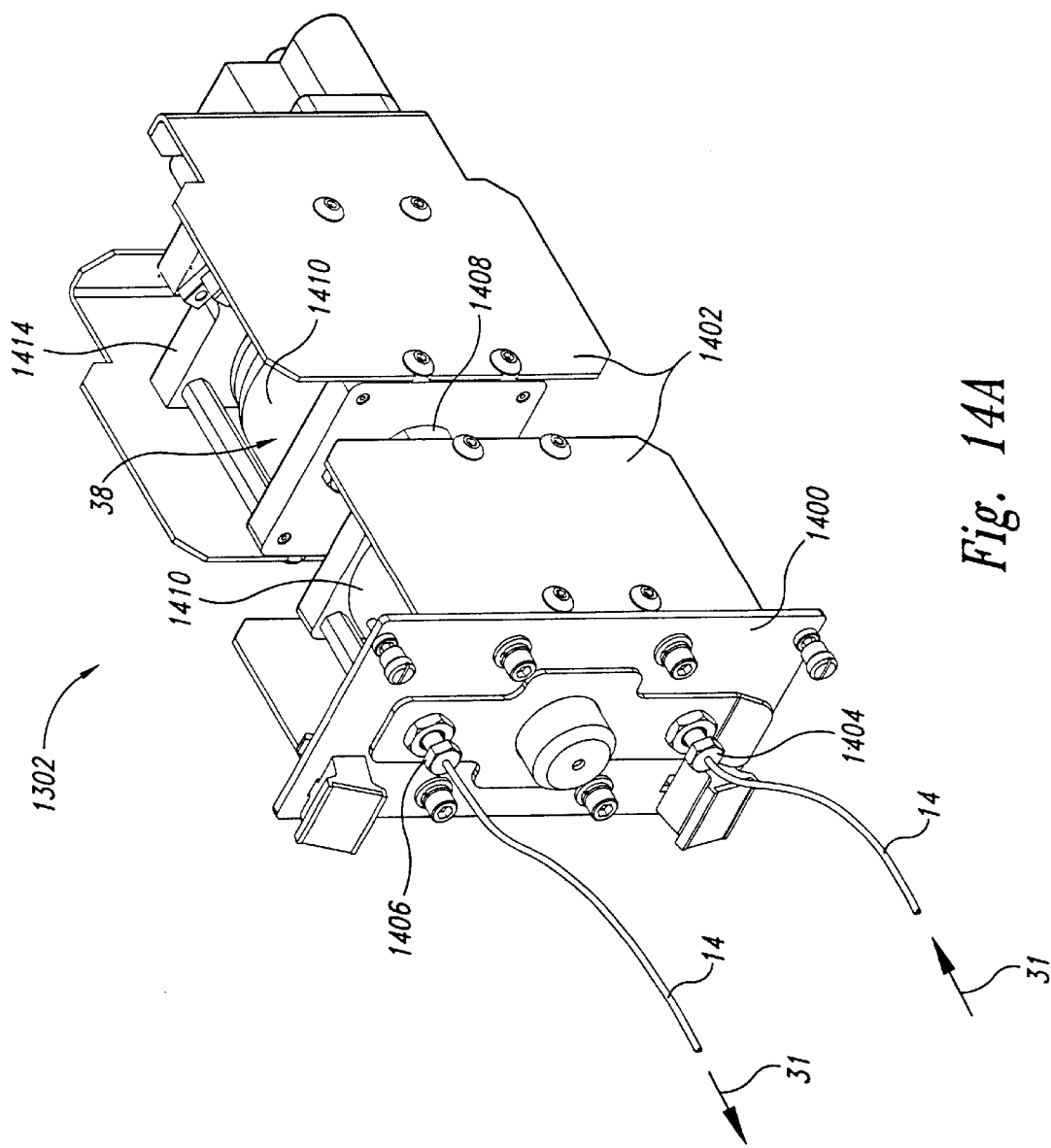
FIG. 14A is an isometric view of a microsample valve from the assembly of FIG. 13.
Figure 14B:
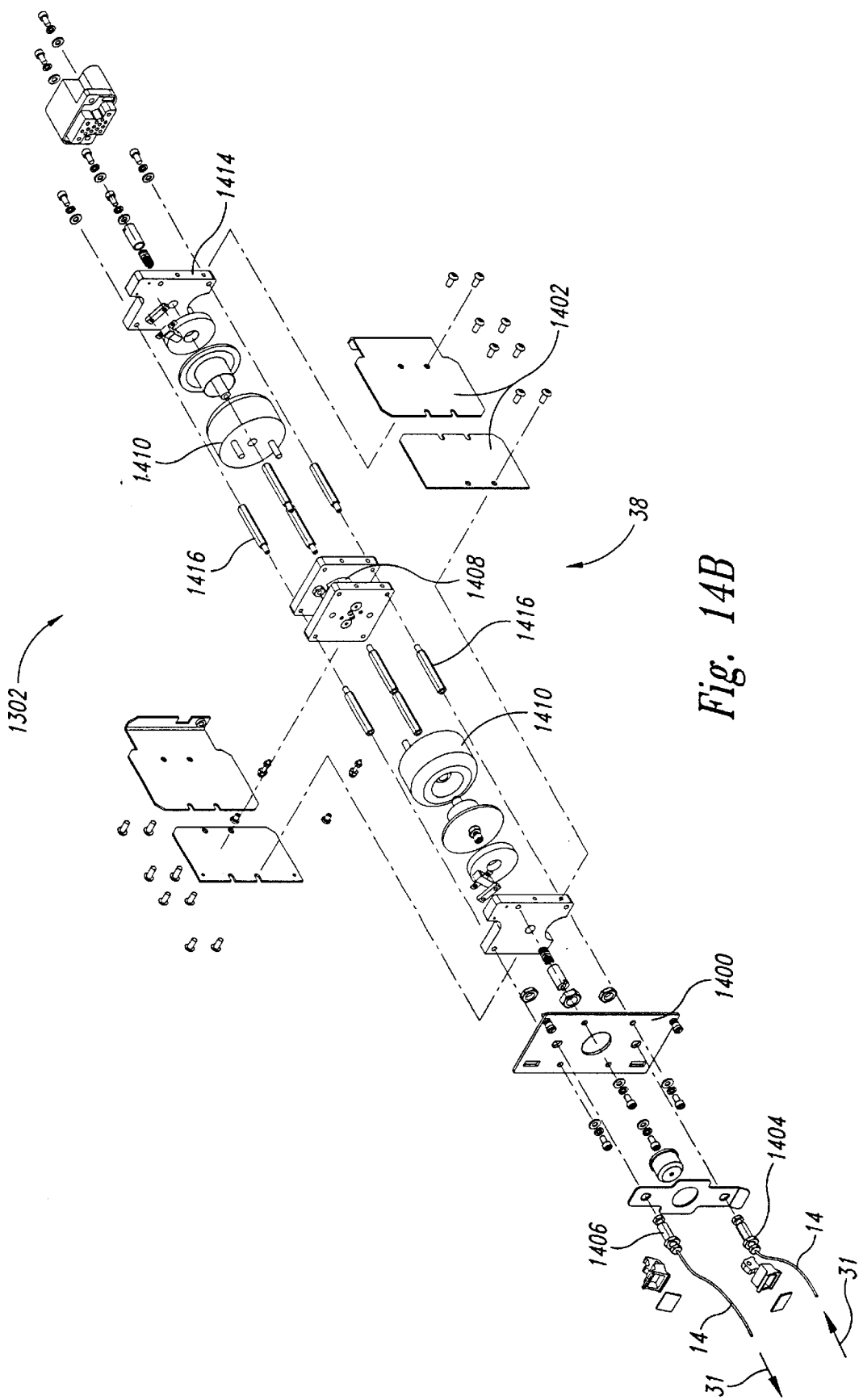
FIG. 14B is an enlarged, exploded isometric view of a microsample valve from the assembly of FIG. 13.

As best seen in FIGS. 14A and 14B, each valve module 1302 includes a faceplate 1400 and opposing side plates 1402 that securely engage the microsample valve 38. The faceplate 1400 has an inlet port 1404 and an outlet port 1406 that receive the purification channel's tubing and direct the sample flow into and out of the valve module 38.

The microsample valve 38 includes a valve body 1408 positioned between a pair of electromagnetic solenoids 1410. The solenoids 1410 are activatable by the computer controller 18 (not shown) to control activation of the microsample valve, as discussed in detail below. The solenoids 1410 are each sandwiched between the valve body 1408 and outer mounting plates 1414, and mounting screws 1416 secure the outer mounting plates to the valve body.

Figure 15:
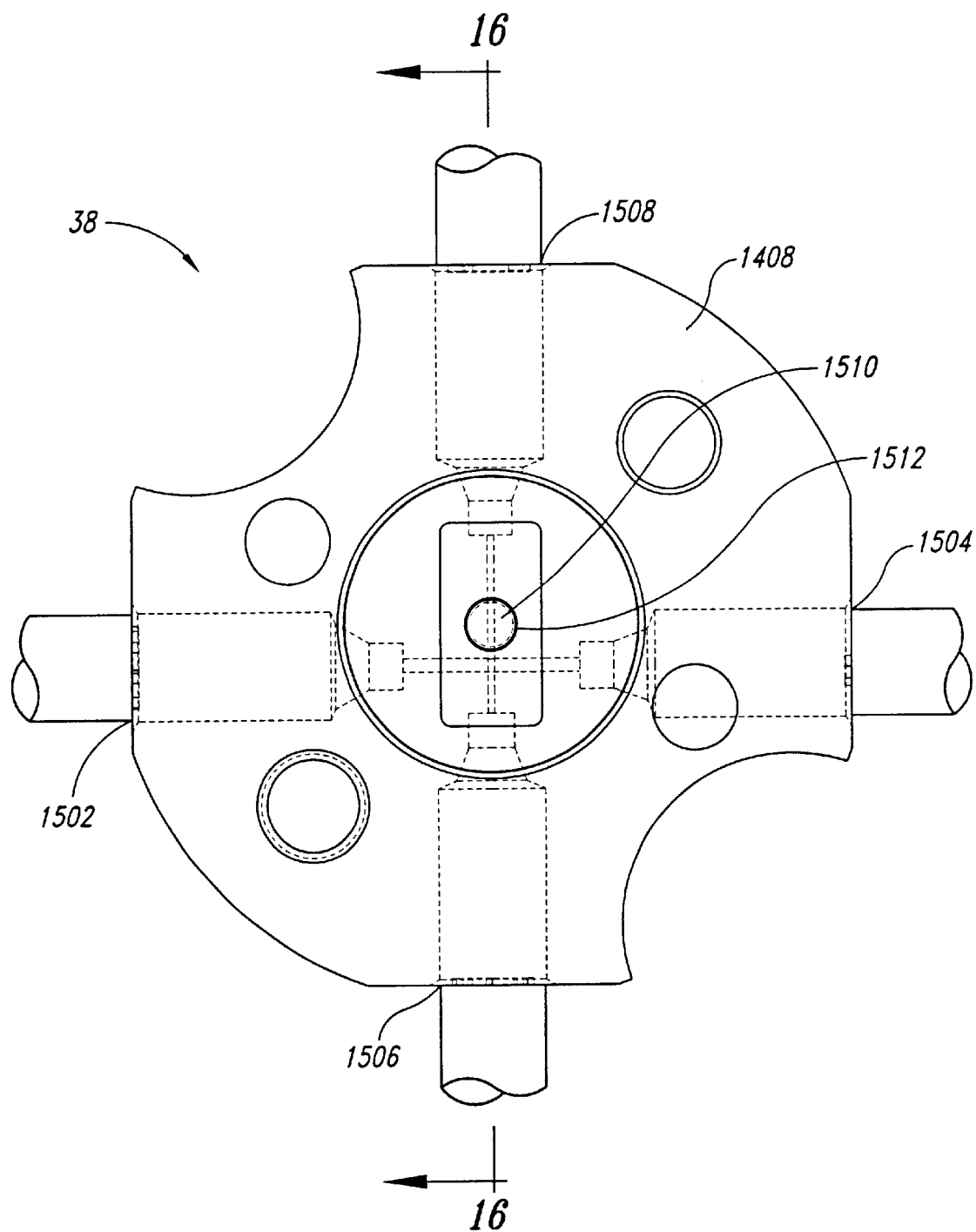
FIG. 15 is a plan view of a valve body of the microsample valve of FIG. 14.
Figure 16:
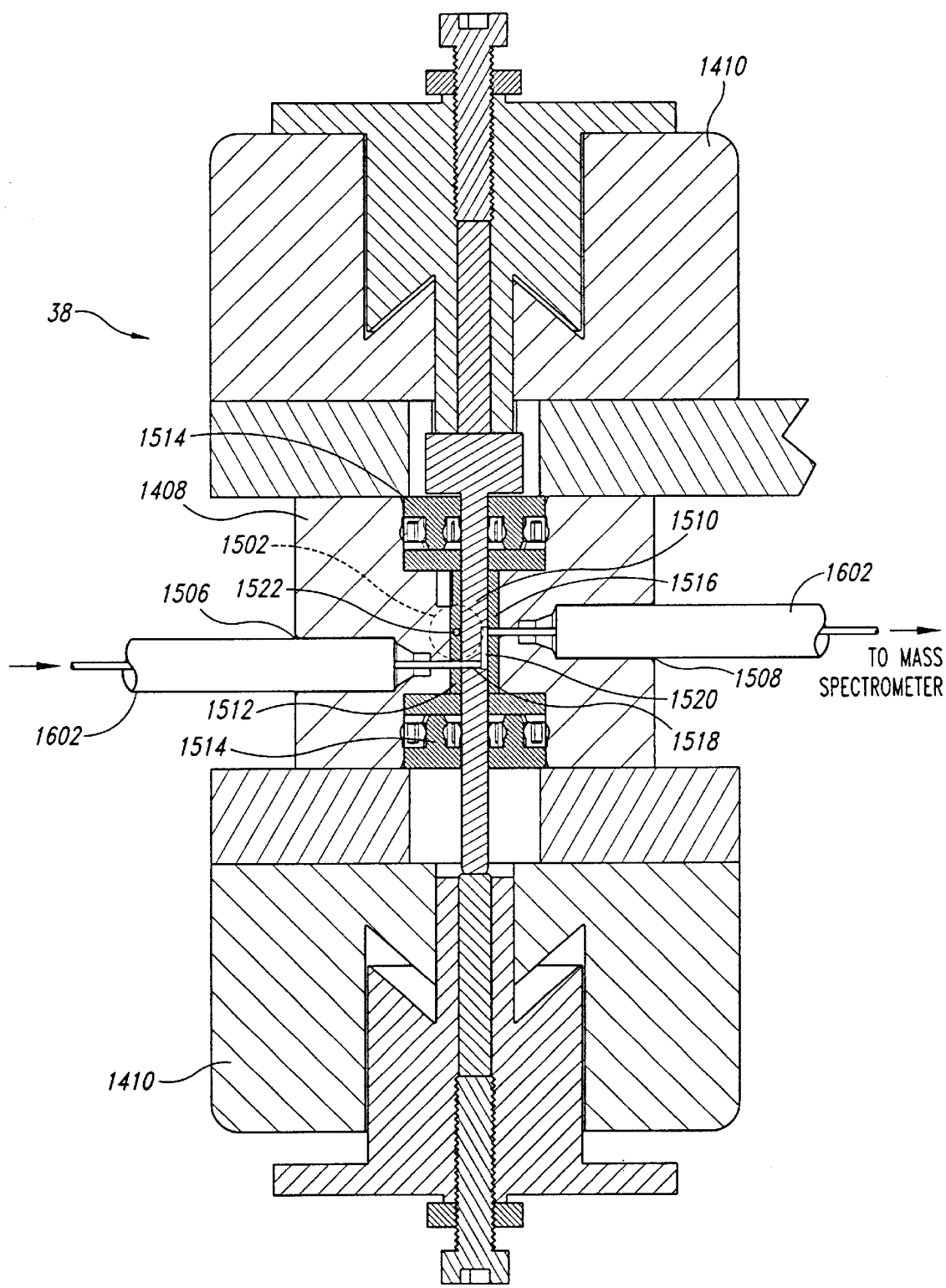
FIG. 16 is an enlarged cross-sectional view taken substantially along line 16—16 of FIG. 14, the microsample valve being shown in a non-sampling position.
Figure 17:
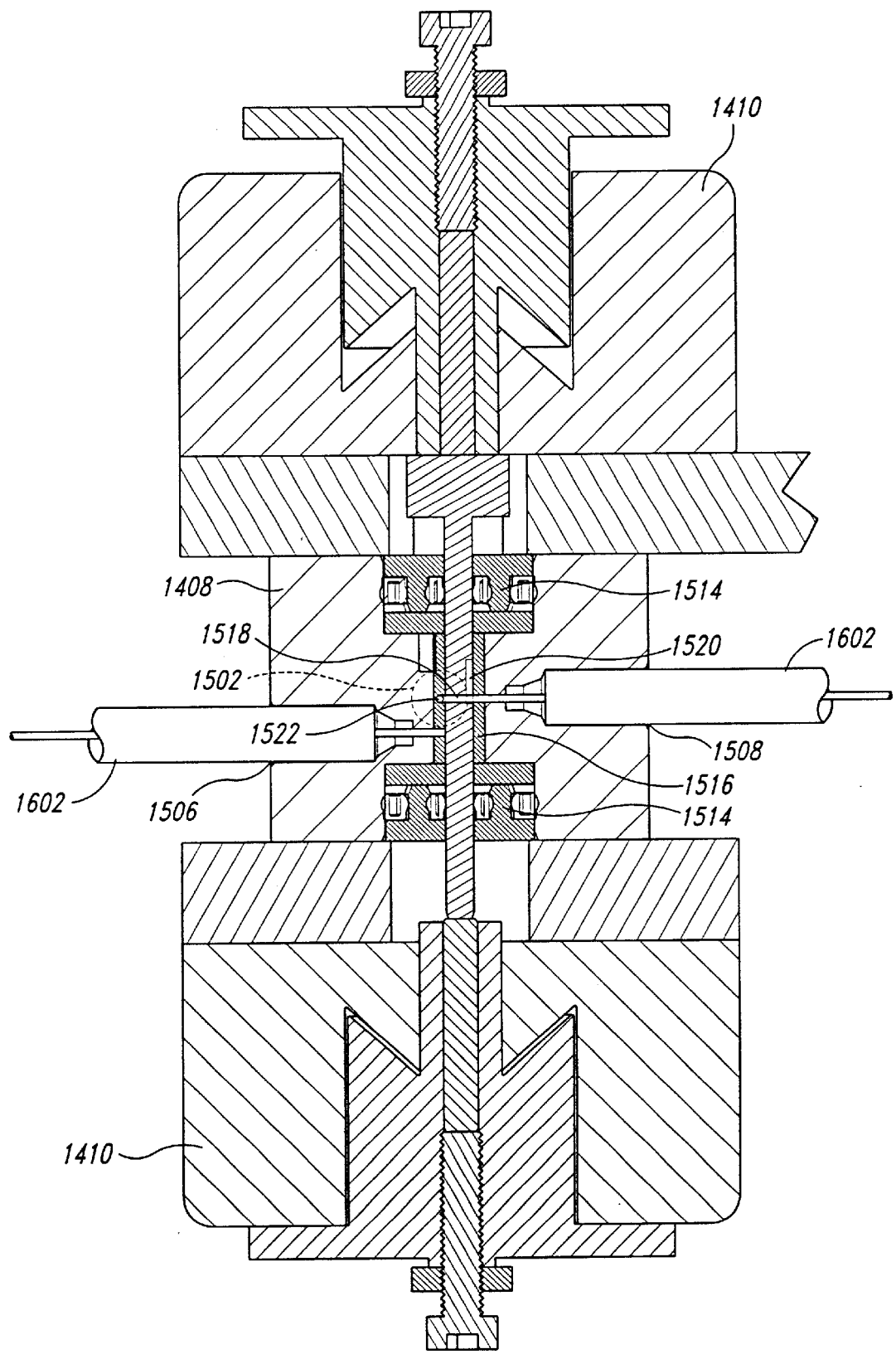
FIG. 17 is an enlarged cross-sectional view taken substantially along line 17—17 of FIG. 14, the microsample valve being shown in a sampling position.

As best seen in FIGS. 15–17, the valve body 1408 has a sample inlet port 1502, a sample outlet port 1504 (FIG. 15), a solvent inlet port 1506, and a flow outlet port 1508. The solvent inlet port 1506 is axially misaligned with the flow outlet port 1508. The flow outlet port 1508 is in fluid communication with the mass spectrometer 16, so fluid exiting the microsample valve 38 through the flow outlet port is carried to the mass spectrometer 16 (FIG. 3). The microsample valve 38 has a stem 1510 slidably disposed within an interior chamber 1512 in the valve body 1408. The stem 1510 slidably extends through the valve body 1408 and is connected at opposite ends to the electromagnetic solenoids 1410. The solenoids 1410 control the stem's axial position within the valve body 1408. The solenoids 1410 are connected to the computer controller 18 (FIG. 3), so the computer controller can control or adjust the stem's axial position. Upper and lower seals 1514 are positioned within the valve body 1408 adjacent to the solenoids 1410, and a center plastic sleeve 1516 extends between the upper and lower seals. The stem 1510 extends through the upper and lower seals 1514 and the plastic sleeve 1516 such that a fluid-tight seal is formed therebetween. In the illustrated embodiments the stem 1510 is press fit into the plastic sleeve 1516, thereby preventing dead space around the stem.

As best seen in FIGS. 16 and 17, the stem 1510 has a through hole 1518 in fluid communication with the flow outlet port 1508 and to the mass spectrometer 16. The stem 1510 also has an axial groove 1520 on the outflow side of the valve body 1408 and in fluid communication with the flow outlet port 1508. The axial groove 1520 extends upwardly from the through hole 1518, along the stem's surface, and is sized to direct the fluid flow upwardly from the through hole along the groove between the stem's surface and the center plastic sleeve 1516. The through hole 1518 is shaped and sized to allow either a flow of carrier solvent or a sampling of a peak from the sample flow to pass toward the mass spectrometer 16.

Referring now between FIGS. 3, 15 and 16, the solvent inlet port 1506 (FIGS. 15 and 16) is connected to a carrier solvent line 1602 that connects to a carrier solvent source 1604 (FIG. 3) and a carrier solvent pump 1606. The carrier solvent pump 1606 is also coupled to the computer controller 18 that controls the flow of carrier solvent to the microsample valves 38. A substantially continuous flow of carrier solvent is provided to the microsample valves 38 during a purification run. In the illustrated embodiment, the carrier solvent line 1602 connects to all four microsample valves 38 in series, so the carrier solvent will flow through all of the microsample valves and to the mass spectrometer 16. Accordingly, the carrier solvent enters the first microsample valve 38 through the solvent inlet port 1506 (FIGS. 15 and 16), exits through the flow outlet port 1508 (FIG. 16), back into the carrier solvent line 1602, and flows into the next microsample valve through its solvent inlet port. The flow continues through each microsample valve 38 and then to the mass spectrometer 16.

The microsample valve 38 in each purification channel 14 also has a continuous flow of the sample flow 31 passing through it. The sample flow 31 enters the microsample valve 38 through the sample inlet port 1502 (FIGS. 15 and 16), through a sample line 1522 extending through the valve body 1408 immediately adjacent to the stem 1510, and out through the sample outlet port 1504. Accordingly, the sample flow 31 in the illustrated embodiment is transverse to the flow of the carrier solvent.

When the microsample valve 38 is in a lowered normal position, shown in FIG. 16, the through hole 1518 is below and out of communication with the sample flow 31. The stem 1510 blocks the sample flow 31 from passing through the flow outlet port 1508 to the mass spectrometer 16 (FIG. 3). When the stem 1510 is in the lowered position, a continuous flow of carrier solvent passes into the valve body 1408 through the solvent inlet port 1506, through the through hole 1518, up the axial groove 1520, and out of the valve body 1408 through the flow outlet port 1508 toward the mass spectrometer 16.

During normal use, when a peak has not been identified, the microsample valve 38 remains in this lowered normal position, so only the carrier solvent flows through the microsample valves to the mass spectrometer 16. When the detector 34 (FIG. 3) detects a peak in the sample flow 31 and the computer controller 18 activates the microsample valve 38, the solenoids 1410 immediately move the stem 1510 axially from the lowered position to a raised sampling position, shown in FIG. 17. In this raised sampling position, the through hole 1518 in the stem 1510 is in fluid communication with the sample line 1522 through which the sample flow 31 travels between the sample inlet and outlet ports 1502 and 1504. Accordingly, the flow of carrier solvent is temporarily interrupted and a small sampling of the peak traveling through the sample line 1522 is diverted from the sample line, through the through hole 1518 to the flow outlet port 1508, and into the carrier line at the location where the carrier solvent flow was interrupted. The sampling then flows to the mass spectrometer 16 (FIG. 3) for analysis.

As the peak is moving past the through hole 1518 at a selected time, as determined by the computer controller 18, the stem 1510 is switched back to the lowered position (FIG. 16). The solenoids 1410 are activated, thereby immediately moving the stem 1510 axially to the lowered position, so the only part of the sample flow 31 received by the mass spectrometer 16 for analysis is the sampling of the peak. When the stem 1510 is returned to the lowered position, the flow of the carrier solvent to the mass spectrometer 16 is resumed. Therefore, the mass spectrometer 16 receives a continuous flow of fluid, and the samplings are effectively inserted as segments of that continuous flow when the microsample valve 38 is activated.

The axial movement of the stem 1510 between the lowered position and the raised sampling position allows for an extremely fast switching between positions, thereby providing for small yet highly accurate samplings of the selected portion of the sample flow. In the illustrated embodiment, the microsample valve 28 is configured to be switched from the normal lowered position, to the raised sampling position and back to the normal lowered position within a time period of approximately 15 to 100 milliseconds, inclusive. In one embodiment the time period is less than 20 milliseconds, so as to divert sample volumes as small as approximately 2 pico liters or less to the mass spectrometer 16. In an alternate embodiment, the microsample valve 28 is configured to be moveable from the normal lowered position, to the raised sampling position and back to the normal lowered position in one second or less. This extremely fast switching also minimizes the chance of cross-contamination within the valve body between samplings of a plurality of peaks within the sample flow.

The microsample valve 38 is designed and constructed so the flow paths through the valve body 1408 and the stem 1510 provide virtually no dead space or unswept volumes that could cause cross-contamination between different samples flowing through the microsample valve. Accordingly, the microsample valve 38 allows for very accurate results in the purification process. The microsample valve 38 is also configured to quickly take the small sample portions from the sample flow, thereby minimizing the pressure drop in the sample flow across the microsample valve 38. In the illustrated embodiment, the pressure drop across the microsample valve is less than approximately 50 psi.

As best illustrated in FIG. 3, the sample flow 31 in each channel 14 moves from the microsample valve 38 to a pressure relief valve assembly 41 that controls the pressure within the flow downstream of the microsample valve. In the illustrated embodiment, the pressure relief valve assembly 41 has the same construction as the back pressure regulator assembly 55 discussed above, except that the heaters are not provided on the back pressure regulator valve. In alternate embodiments, the heaters can be used if needed as a result of ice formation or larger pressure drops experienced in the system. In other alternate embodiments, other back pressure regulators can be used, provided they are durable enough and provide sufficient pressure control for the purification valve.

The use of the pressure relief valve 41 allows the flow volume to the analyzer to be very small because of either use of a small bore capillary to the analyzer or an active back-pressure regulator. Accordingly, the pressure differential is reduced and the flow volume to the mass spectrometer 16 is reduced.

The sample flow 31 exits the pressure relief valve assembly 41 and flows to two flow directing valves, referred to as a fraction collection valve assemblies 40 with first and second collection valves 40a and 40b for each channel. Each fraction collection valve assembly 40 has, for each channel, one inlet port 42, two outlet ports 44 and 46 for collection, and a waste port 47. The inlet port 42 is coupled to both of the first and second collection valves 40a and 40b, and each outlet port 44 and 46 is connected to a respective one of the first or second collection valves. Each of the first and second collection valves 40a and 40b are also operatively coupled to the computer controller 18. When a portion of the sample flow 31 containing a peak enters the fraction collection valve assembly 40 through the inlet port 42, as identified by the computer controller 18, the computer controller activates the first or second fraction collection valve 40a and 40b to control whether the peak in the sample flow is directed out of the first outlet port 44 or the second outlet port 46.

If the mass spectrometer 16 determines that the peak is the target compound, the computer controller 18 activates the first collection valve 40a, so the collection valve moves to a first position. In this position, the sample portion containing the peak is directed out of the first collection valve 40 through the first outlet valve 44. The sample portion is directed to a fraction collector assembly 43 and is collected directly into a predetermined location in a selected well of the first receiving microtiter plate 22.

When a portion of a sample flow containing a peak passes through the fraction collection valve assembly 40, and that peak is a reaction by-product rather than the target compound, the second collection valve 40b is switched to direct a portion of the sample flow through the second outlet port 46. This portion of the sample flow 31 exits the second outlet port 46, passes through the fraction collection assembly 43 and is collected directly into a selected well of the second receiving microtiter plate 24. When a portion of the sample flow 31 passes through the fraction collection valve and that portion does not contain any peaks, the sample flow passes through the waste outlet 47 and is carried to a waste receptacle 52.

The purification system 10 of the exemplary embodiment allows the purified samples to be automatically dispensed into selected wells of the receiving microtiter plate 22 or 24, where each sample is dispensed into a well having the same relative location in the receiving microtiter plate as the supply microtiter plate well from which the sample was initially drawn to begin the purification run. Therefore, the purified target compound is deposited directly into a well having a one-to-one corresponding well address as the original sample well. Similarly, the purified reaction by-products are deposited directly into a well having a corresponding well address and the second receiving microtiter plate, so the reaction by-products are collected separately from the purified target compounds. This direct depositing of the target compounds into a selected microtiter plate well avoids further processing and formatting before the purified target compounds are put into microtiter plates. Accordingly, the efficiency of the purification process is increased and the time and cost requirements are decreased.

This purification system 10 of the illustrated embodiment results in the collection of purified compounds having an 85% purity or better. It is preferred, of course, to provide samples having purity as close to 100% pure as possible. Upon collection of the purified target compounds in the receiving microtiter plate 22, these purified target compounds are ready for a screening process or other selected process.

Figure 20:
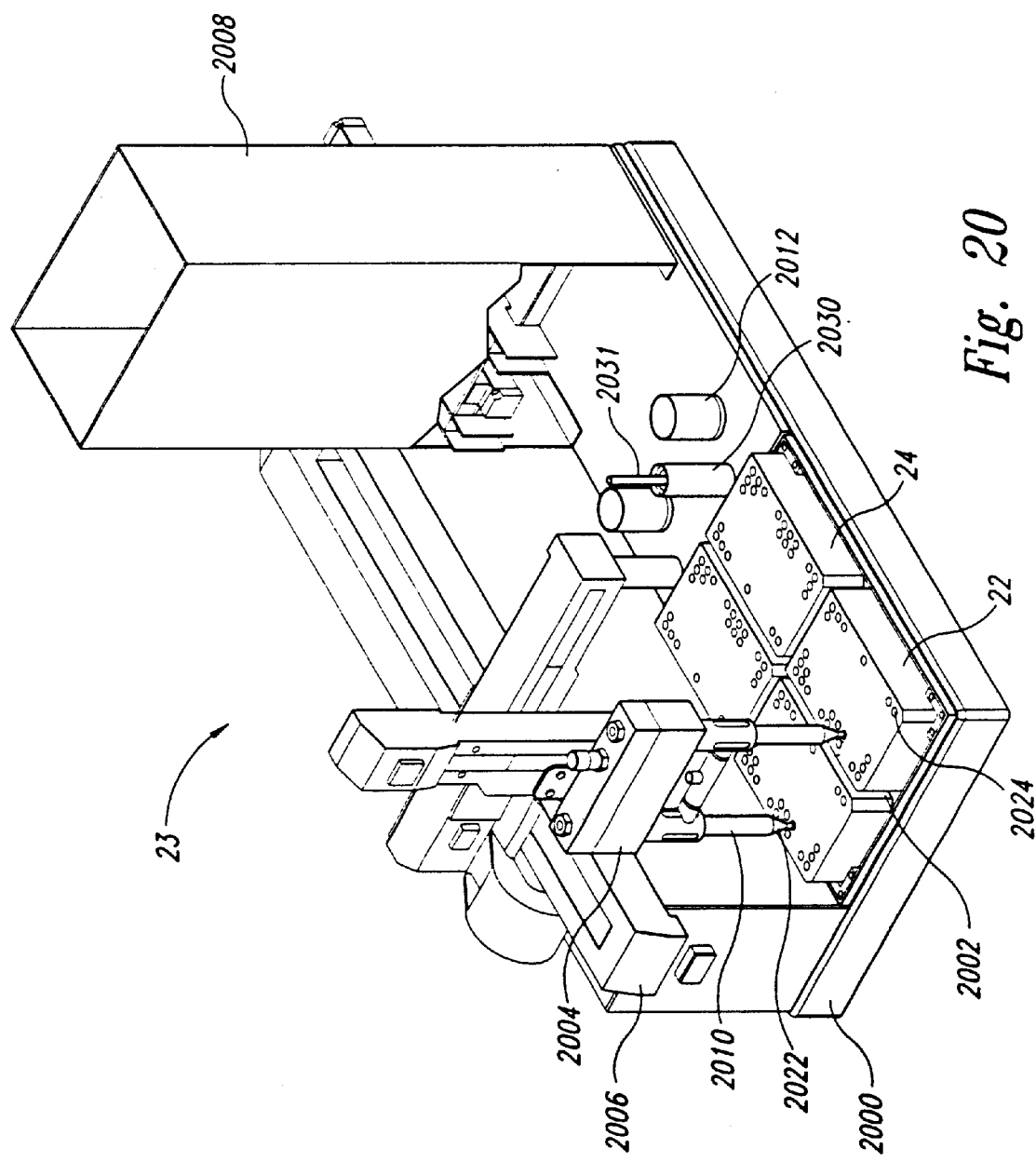
FIG. 20 is an isometric view of the fraction collection assembly of FIG. 19 shown in a collection position.

As best seen in FIG. 20, the fraction collector assembly 43 includes a frame 2000 that supports a docking station 2002 that removably receives the receiving microtiter plates 22 and 24. The fraction collector assembly 43 also includes a dispensing head 2004 that travels laterally along a rail 2006 mounted to the frame 2000 between several operating positions, discussed below.

The fraction collector assembly 43 includes a hopper 2008 that contains clean, disposable expansion chambers 2010. The fraction collector assembly 43 is configured to provide the expansion chambers 2010 from the hopper 2008 to a pickup station 2012. The pickup stations 2012 holds the expansion chambers 2010 in a substantially vertical orientation with an open top end 2020 of the expansion chamber facing upwardly. The dispensing head 2004 is moveable to a position over the pickup station 2012 and moveable downwardly so dispensing needles 2014 on the dispensing head 2004 extend into the expansion chambers. The dispensing head 2004 then grasps the expansion chambers 2010 and lifts them from the pickup station 2012.

Figure 21:
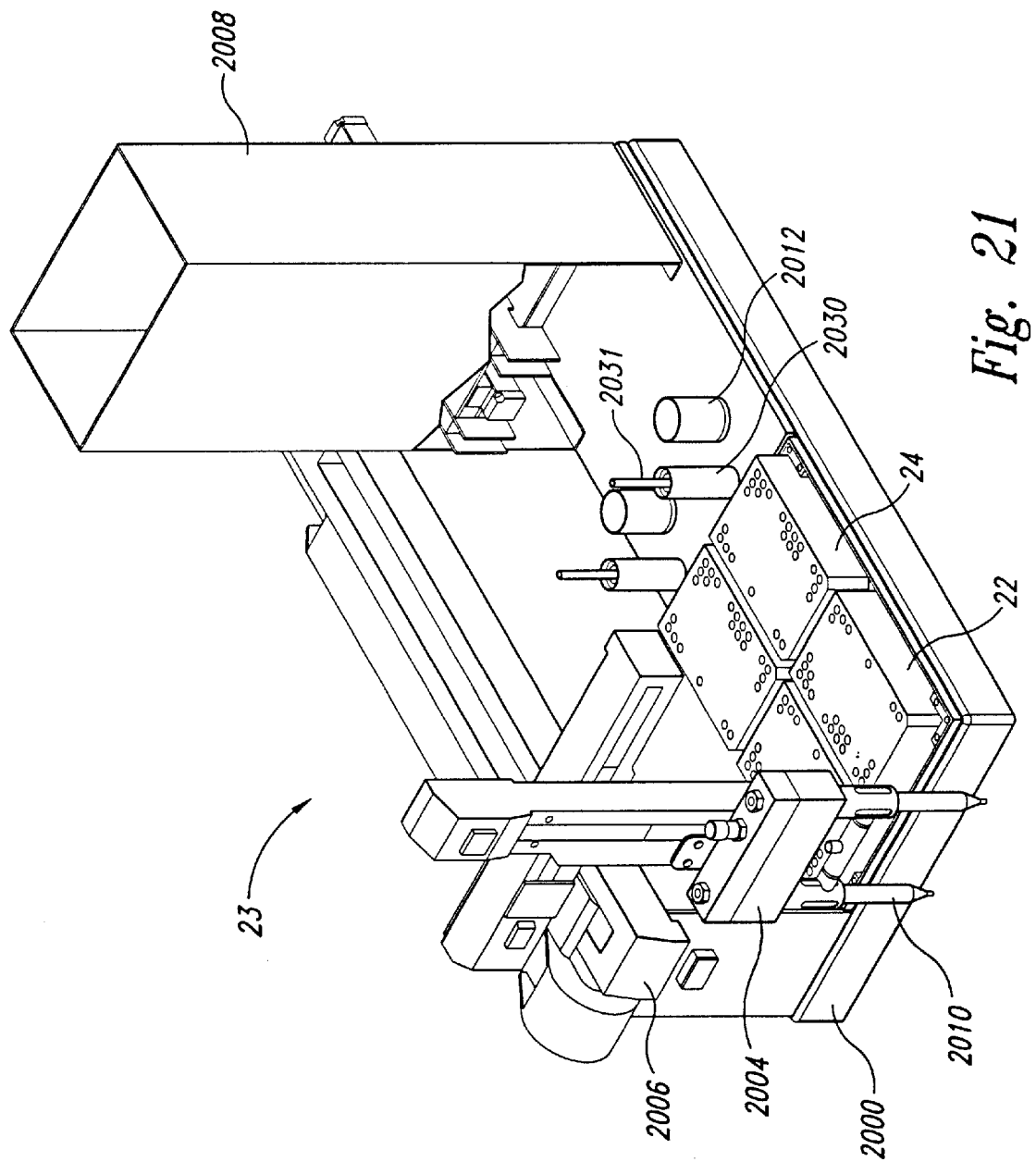
FIG. 21 is an isometric view of the fraction collection assembly of FIG. 19 shown in a chamber drop-off position.

As best seen in FIG. 21, the dispensing head 2004 moves the expansion chambers 2010 from the pickup station 2012 to a dispensing position over selected wells 2024 in the microtiter plates 22 and 24. The dispensing head 2004 is coupled to the computer controller 18 that controls the positioning of the expansion chambers 2010 over the wells 2024 so as to correspond to the well locations from which the sample was originally taken. The dispensing head 2004 moves the expansion chambers 2010 downwardly so as to extend at least partially into the selected wells 2024. Once the expansion chamber 2010 is lowered, the sample portion containing either the target or the reaction by-product is deposited from the dispensing needle 2014, into the expansion chamber 2010, and into the selected well 2024 in the microtiter plate 22 or 24.

Figure 18:
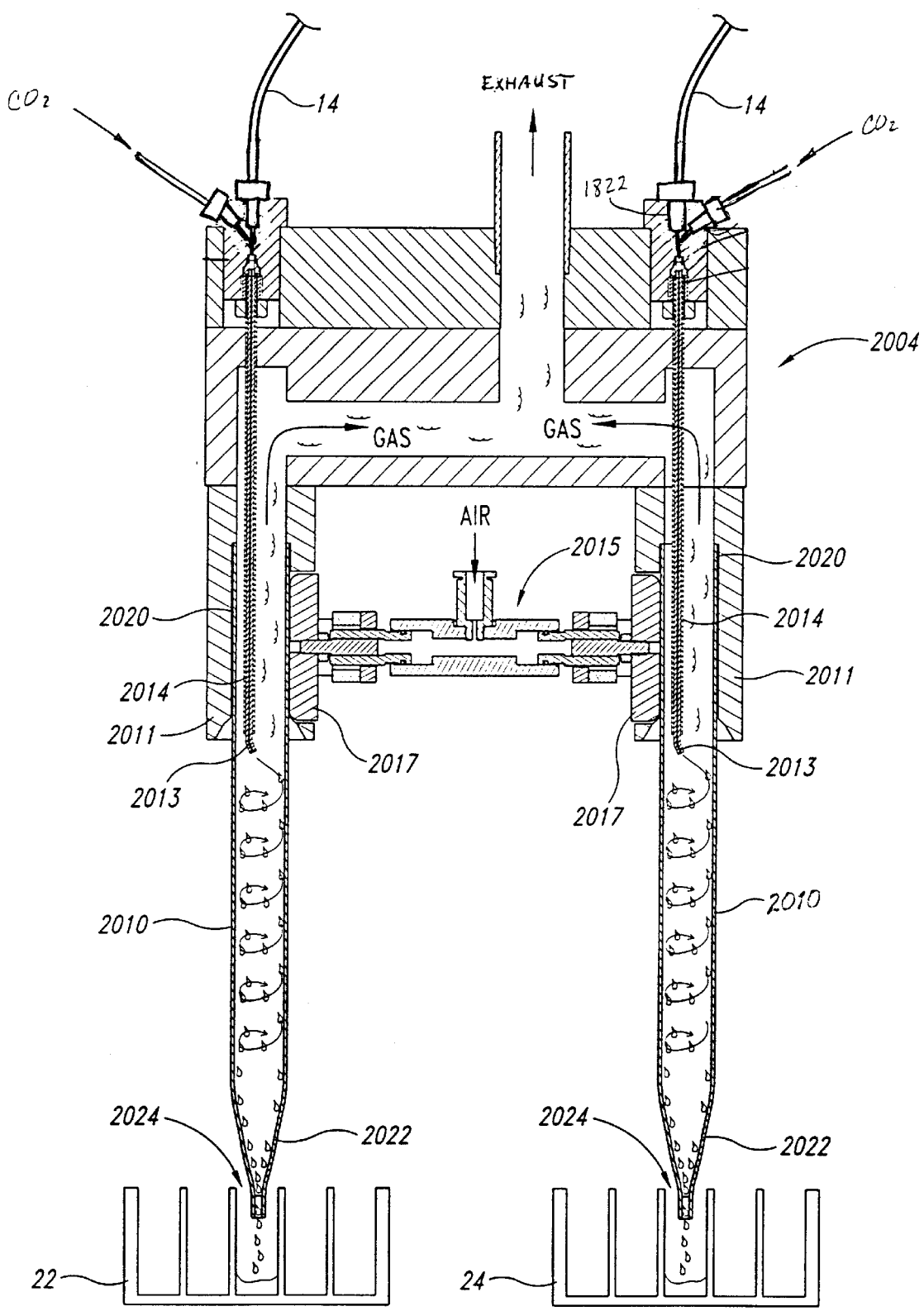
FIG. 18 is an enlarged cross-sectional view of a dispensing head and an expansion chamber from the purification system of FIG. 3, the dispensing head being shown in a dispensing position.

As best seen in FIG. 18, the dispensing head 2004 of the illustrated embodiment releasably holds two expansion chambers 2010 in tubular holding members 2011. A pneumatic gripping assembly 2015 is connected to each tubular holding member 2011 in a position to releasably engage the expansion chambers 2010. The gripping assembly 2015 includes a pair of grippers 2017 connected to pneumatic cylinders 2019. The pneumatic cylinders 2019 move the grippers 2017 relative to the tubular holding member 2011 between holding and released positions. In the holding position, each gripper 2017 presses the expansion chamber 2010 against the tubular holding member 2011, so the expansion chamber is frictionally held in the tubular holding member. In the released position, each gripper 2017 is positioned to allow the respective expansion chamber 2010 to freely move into or out of the tubular holding member 2011.

The expansion chamber 2010 is a tubular member having the open top end 2020 that is releasably engaged by the gripping assembly 2015 of the dispensing head 2004, and a tapered, open bottom end 2022. The open bottom end 2022 is positionable partially within a selected well 2024 of the microtiter plate 22 or 24. The expansion chamber's open top end 2020 is positioned so the dispensing needle 2014 extends therethrough into the expansion chamber's interior area 2028. The dispensing needle 2014 is positioned adjacent to the expansion chamber's sidewall so the needle is not coaxially aligned with the expansion chamber. The distal end 2013 of the dispensing needle 2014 is angled so as to point toward the respective expansion chamber's sidewall.

Before the sample is dispensed into the expansion chamber 2010, a stream of high pressure liquid carbon dioxide is directed through the dispensing needle and against the sidewalls of the expansion chamber. The carbon dioxide chills the sidewalls of the expansion chamber to facilitate collection of the fractions. As the sample portion is dispensed from the dispensing needle 2014 into the interior area 2028 of the expansion chamber 2010, the sample portion is in an atomized state. The atomized sample portion enters the expansion chamber 2010 through the needle's angled distal end 2013, and the distal end direct the flow toward the expansion chamber's sidewall. The atomized sample portion condenses on the expansion chamber's chilled sidewalls as a liquid, and is directed so the condensed liquid moves along the sidewalls in a downwardly spiral direction.

The condensed, non-atomized liquid sample portion flows out of the open expansion chamber's bottom end 2022 into the selected well 2024 in the microtiter plate 22 or 24. As the atomized sample portion is being dispensed into the expansion chamber 2010, the $CO_2$ vapor exits the expansion chamber through its open top end 2020. In the illustrated embodiment, a vacuum is drawn within the expansion chamber to draw the $CO_2$ vapors out and away from the expansion chamber's open top end 2020, thereby avoiding cross-contamination between channels.

As the sample portion is condensed in the expansion chamber 2010, some of the liquid sample portion may remain in the bottom of the expansion chamber because of a capillary action at the narrow open bottom end 2022. At this point, the fraction collection valve dispenses a selected solvent into the expansion chamber to rinse it out and carry any remaining sample into the microtiter plate 22 or 24.

After the sample portion has been fully dispensed, the dispensing head 2004 can provide a puff of low pressure air into the expansion chamber 2010. The air forces the remaining liquid sample out of the expansion chamber 2010 and into the well 2024.

As best seen in FIG. 21, after the sample has been dispensed into the microtiter plate 22 or 24, the dispensing head 2004 moves to a chamber drop-off position so the expansion chambers 2010 are positioned past the edge of the frame 2000. The gripping assembly 2015 of the dispensing head 2004 moves to the released position and the expansion chambers 2010 drop into a suitable waste receptacle. In one embodiment, the expansion chambers 2010 are thrown away. In an alternate embodiment, the expansion chambers 2010 are recycled so as to be reusable.

Figure 19:
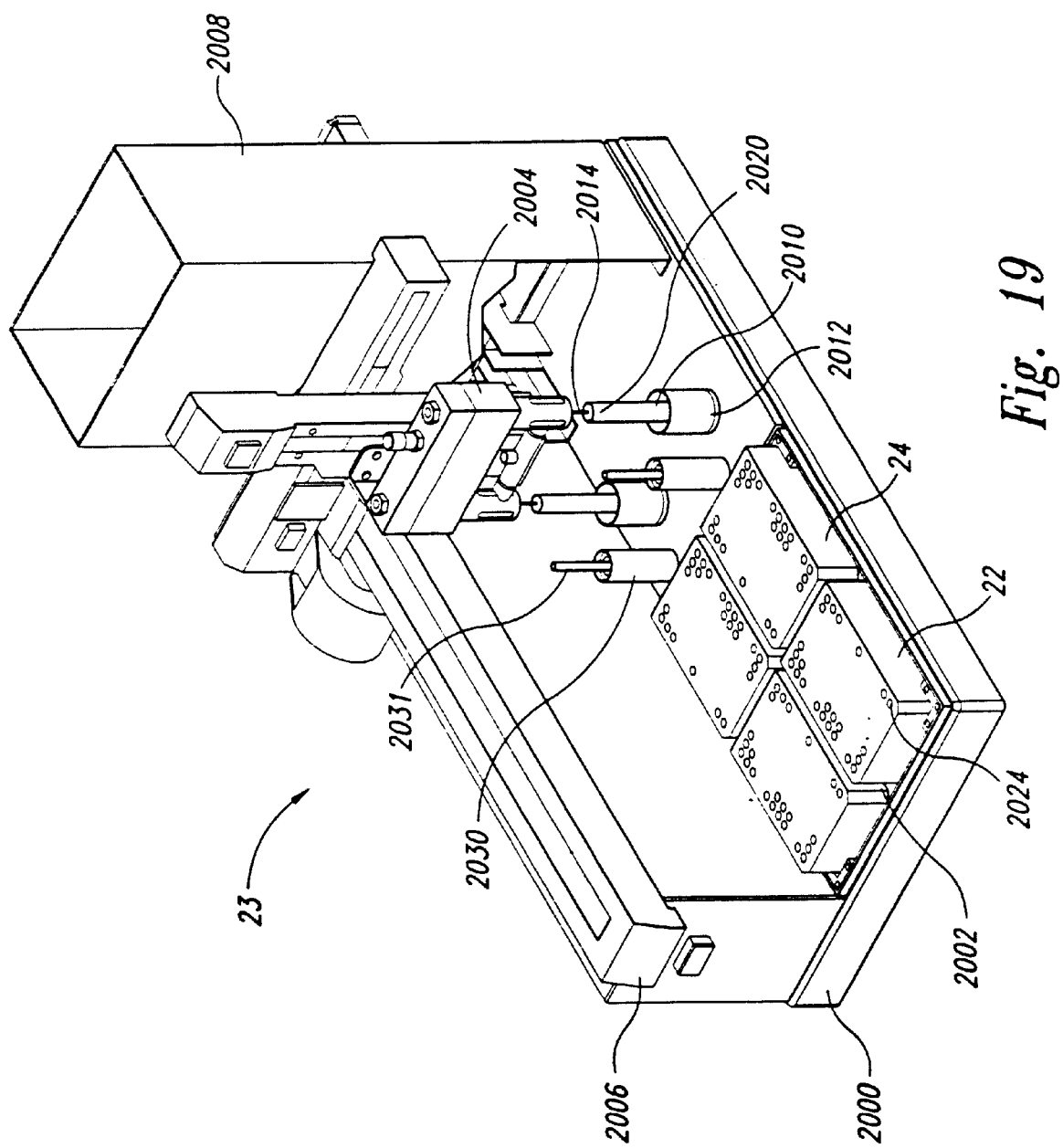
FIG. 19 is an isometric view of an automated fraction collection assembly of the purification system of FIG. 3, the assembly shown in a chamber pickup position.
Figure 22:
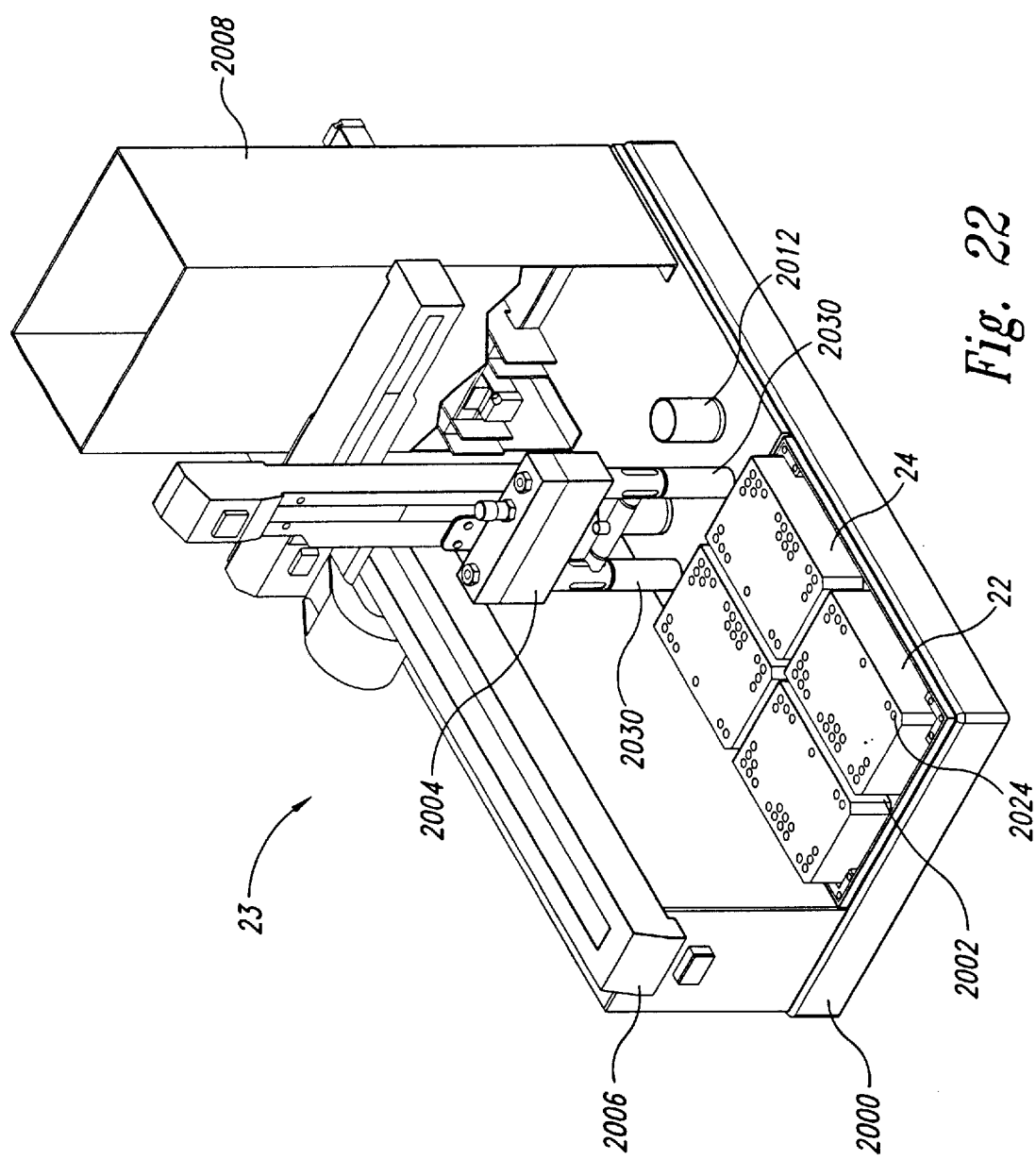
FIG. 22 is an isometric view of the fraction collection assembly of FIG. 19 shown in a rinse position.

After the dispensing head 2004 drops off the expansion chambers, the dispensing head moves to a needle rinse position, illustrated in FIG. 22. In this needle rinse position, the dispensing head 2004 is positioned over a pair of wash stations 2030. As seen in FIGS. 19–21, the wash stations 2030 each include a wash tube 2031 that dispenses a cleaning solvent or other solution. The wash tubes 2031 are sized and positioned so the dispensing head 2004 can lower the dispensing needles 2014 into the wash tube 2031. The wash station 1230 is then energized and dispenses cleaning fluid onto the outside of the dispensing needles 2014. The dispensing head 2004 is then raised washing the dispensing needles 2014 from the top to the bottom as they are withdrawn from the wash tube 2031. The dispensing head 2004 is then moved back to the expansion chamber pickup position, illustrated in FIG. 20, wherein new expansion chambers are picked up and ready for dispensing other sample portions into the microtiter plates 22 and 24.

The high throughput purification system 10 of the illustrative embodiment allows for relatively fast sample purification as compared to conventional purification processes. A purification run of a selected sample can be accomplished in approximately 6–8 minutes or faster. Therefore, purification of samples contained in a 96 well microtiter plate will take approximately 144–192 minutes. Purification of 4,000 samples generated in a week using sample generation techniques, discussed above, will only take in the range of 250–330.3 hours, as opposed to the 2,000 hours required to purify the 4,000 samples, using conventional purification techniques. Therefore, the high throughput purification system in accordance with the present invention allows for a significant increased speed of purification. This system also provides for collecting the purified samples directly into a microtiter plate in wells having a location address corresponding to the location address of the well in the microtiter plate from which the samples were originally drawn. Thus, the purified compounds are ready to be screened or otherwise processed. The result is a significantly increased capacity for purification that allows for a less expensive purification process.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A pressure regulator assembly usable in a high throughput fluid system having a fluid channel for carrying a fluid flow therethrough, comprising:

an inlet line and an outlet line connectable to the fluid channel;

a regulator body having a regulator inlet and outlet, the regulator inlet connected to the inlet line and the regulator outlet connected to the outlet line, the regulator body having a chamber therein in fluid communication with the regulator inlet and outlet;

a nozzle in fluid communication with the regulator inlet, the nozzle having a nozzle outlet adjacent to the chamber;

a stem axially aligned with the nozzle outlet, the stem having one end forming a regulating surface and another end forming a mounting portion, the regulating surface being positioned adjacent to the nozzle outlet and being positioned to restrict the fluid flow through the chamber to the regulator outlet;

a mounting rod attached to the stem's mounting portion, the mounting rod and stem being axially moveable in the regulator body relative to the nozzle outlet; an adjustment member connected to the mounting rod and being axially moveable to adjust the position of the stem relative to the nozzle outlet, the adjustment member having a dual concentric thread arrangement with first and second threads, the first threads engaging the mounting rod and being configured to move the mounting rod and stem as a unit in a first direction and at a first rate relative to the nozzle outlet and the second threads being configured to move the adjustment member, the mounting rod, and the stem as a unit in a second direction and at a second rate relative to the nozzle outlet, the second direction being opposite the first direction, and the first rate being different than the second rate to provide an attenuated movement of the stem's regulating surface relative to the nozzle outlet to selectively adjust a pressure of the fluid flow in the chamber; and a drive mechanism connected to the adjustment member and positioned to rotate the adjustment member for axial adjustment of the stem.

2. The pressure regulator assembly of claim 1 wherein the nozzle has a body portion with a cavity formed therein, the nozzle insert is retained in the body portion's cavity, the body portion being a first material, the nozzle insert is a second material.

3. The pressure regulator assembly of claim 2 wherein the nozzle insert is one of a ruby, sapphire, and diamond.

4. The pressure regulator assembly of claim 1, further comprising a biasing member positioned to bias the stem toward the nozzle.

5. The pressure regulator assembly of claim 1 wherein the stem is made of one of ruby, sapphire, and diamond.

6. The pressure regulator assembly of claim 1 wherein the adjustment member has a threaded axial aperture that receives the mounting rod therein, the first threads are internal threads in the axial aperture, and the second threads are external threads on an outer surface of the adjustment member.

7. The pressure regulator assembly of claim 1 wherein the first threads have a first thread pitch, and the second threads have a second thread pitch, the first thread pitch being greater than the second thread pitch.

8. The pressure regulator assembly of claim 1 wherein the first and second threads are both right-handed pitch threads.

9. The pressure regulator assembly of claim 1 wherein the second threads engage the regulating body.

10. The pressure regulator assembly of claim 1 wherein the drive mechanism is a stepper motor that rotationally drives the adjustment member.

11. The pressure regulator assembly of claim 1 wherein the high throughput fluid system is a supercritical fluid chromatographic purification system and the inlet and outlet lines, the regulator inlet and outlet, the chamber, nozzle, and stem are shaped and sized for directing a flow of pressurized supercritical fluid flow therethrough.

12. The pressure regulator assembly of claim 1, further comprising a seal positioned in the chamber and sealably engaging the stem at a position spaced apart from the stem's regulating surface.

13. The pressure regulator assembly of claim 1, further including a rotational travel stop positioned to block movement of the stem past a preselected position relative to the regulator body.

14. The pressure regulator assembly of claim 1, further comprising a heater assembly connected to the regulator body and engaging a portion of the outlet line, the heater assembly being positioned to heat a portion of the fluid flow in the outlet line to provide heat to the fluid flow after the fluid flow has exited the regulator outlet.

15. The pressure regulator assembly of claim 14 wherein the heater assembly includes a heat transfer body connected to the regulator body and a heater band attached to the heat transfer body, the heat portion of the outlet line being wrapped around the transfer body.

16. A pressure regulator assembly usable in a high throughput fluid system having a fluid channel for carrying a fluid flow therethrough the fluid channel having an inlet line and an outlet line, comprising:
- a regulator body having a regulator inlet and outlet, the regulator inlet being coupleable to the fluid channel's inlet line and the regulator outlet being coupleable to the fluid channel's outlet line, the regulator inlet and outlet being sized to carry the fluid flow into and out of the regulator assembly, respectively, the regulator body having a chamber therein in fluid communication with the regulator inlet and outlet;
- a nozzle fluid communication with the regulator inlet and positioned to receive the fluid flow from the regulator inlet, the nozzle having a nozzle outlet in fluid communication with the chamber to direct the fluid flow to the chamber;
- a regulating mechanism adjustably connected to the regulator body, the regulating mechanism having a mounting portion and regulating surface, the regulating surface being positioned in the chamber adjacent to the nozzle outlet, the regulating surface being spaced apart from the nozzle outlet and being positioned to restrict the fluid flow through the chamber to the regulator outlet;
- an adjustment member connected to the regulating mechanism's mounting portion and being movably retained in the regulator body, the adjustment member being moveable to adjust the position of the regulating mechanism's regulating surface relative to the nozzle outlet, the adjustment member having first and second adjusting portions, the first adjusting portion engaging the regulating mechanism and being moveable to move the regulating surface in a first direction and at a first rate relative to the nozzle outlet when the adjustment member moves a selected distance, and the second adjusting portion being moveable to move the regulating surface in a second direction and at a second rate, the second direction being opposite the first direction, and the first rate being different than the second rate to provide an attenuated movement of the regulating surface relative to the nozzle outlet to selectively adjust a pressure of the fluid flow in the chamber; and
- a drive mechanism connected to the adjustment member and positioned to move the adjustment member relative to the regulator body for adjustment of the pressure of the fluid flow moving to the regulator outlet.

17. The pressure regulator assembly of claim 16 wherein the nozzle has a body portion with a cavity formed therein, the body portion being a first material, and a nozzle insert is retained in the body portion's cavity and in direct communication with the chamber, the nozzle insert being made of a second material different than the first material.

18. The pressure regulator assembly of claim 17 wherein the second material is one of ruby, sapphire, and diamond.

19. The pressure regulator assembly of claim 16 wherein the regulating mechanism includes a stem axially aligned with the nozzle outlet, the stem having first and second end portions, the first end portion forming the regulating surface, the regulating mechanism having a mounting rod attached to the stem's second end portion, the mounting rod being connected to an adjustment shaft having an end portion forming the regulating mechanism's mounting portion.

20. The pressure regulator assembly of claim 19 wherein the mounting rod is axially moveable relative to the adjustment shaft and a biasing member biases the mounting rod toward the nozzle.

21. The pressure regulator assembly of claim 19 wherein the stem is made of one of ruby, sapphire, and diamond.

22. The pressure regulator assembly of claim 16 wherein the regulating body has a threaded aperture therein, the mounting portion of the regulating mechanism has threads thereon, and the adjustment member having a shaft portion with the first and second adjustors thereon, the first adjustor being first threads and the second adjustor being second threads concentrically arranged relative to the first threads, the first threads having first pitch, and the second threads having a second pitch different than the first pitch, the threads on the mounting portion engaging the first threads of the shaft portion, the second threads on the shaft portion engaging the regulator body in the threaded aperture, the shaft portion of the regulating mechanism being rotatable relative to the mounting portion and the regulator body, the first and second threads having directional orientations relative to each other wherein rotation of the regulating mechanism's shaft portion moves the shaft portion axially in one direction at a first rate relative to the regulator body, and the rotation moves the regulating mechanism in an opposite direction and at a second rate different than the first rate.

23. The pressure regulator assembly of claim 22 wherein the first and second adjustors are first and second threads concentrically arranged relative to each other, the first threads having a first pitch and the second threads having a second pitch different than the first pitch, the first threads engage the regulating mechanism.

24. The pressure regulator assembly of claim 22 wherein the first thread pitch is greater than the second thread pitch.

25. The pressure regulator assembly of claim 22 wherein the first and second threads are both right-hand pitch threads oriented in opposing directions to form a dual concentric adjustment screw configuration.

26. The pressure regulator assembly of claim 22 wherein the second threads engage the regulating body.

27. The pressure regulator assembly of claim 22 wherein the drive mechanism is a stepper motor that rotationally drives the adjustment member.

28. The pressure regulator assembly of claim 16, further comprising a seal positioned in the chamber and sealably engaging the regulating member at position spaced apart from the regulating surface.

29. The pressure regulator assembly of claim 16, further including a rotational travel stop connected to the adjustment mechanism and positioned to block the adjustment mechanism from moving past a pre-selected position relative to the regulator body, thereby blocking the regulating mechanism from contacting the nozzle.

30. The pressure regulator assembly of claim 16, further comprising a filter positioned to receive and filter the fluid flow before the fluid flow enters the regulator inlet.

31. The pressure regulator assembly of claim 16, further comprising a heater assembly connected to the inlet regulator body and positionable adjacent to the outlet line of the fluid channel, the heater assembly being positioned to heat a portion of the outlet line to provide heat to the fluid flow after the fluid flow has exited the regulator outlet.

32. The pressure regulator assembly of claim 31 wherein the heater assembly includes a heat transfer body connected to the regulator body and a heater band attached to the heat transfer body, the heat transfer body having a receiving surface that receives the outlet line therearound.

33. The pressure regulator assembly of claim 16 wherein the nozzle and the regulating surface are made of a selected material for use with selected caustic solvents and at pressures of approximately 2000 psi or greater.

34. A pressure regulator assembly usable in a high throughput fluid purification system having a fluid channel for carrying a selected fluid flow therethrough, comprising:
- a regulator body having a regulator inlet and outlet coupleable to the fluid channel, the regulator inlet and outlet having fluid passages therethrough sized to carry the selected fluid into and out of the regulator assembly, the regulator body having a threaded aperture therein;
- a nozzle having a nozzle passage in fluid communication with the fluid passage in the regulator inlet and positioned to receive the selected fluid flow from the regulator inlet, the nozzle passage having a nozzle inlet that receives the selected fluid flow into the nozzle, and a nozzle outlet through which the fluid flow exits the nozzle, the nozzle outlet being in fluid communication with a pressure control chamber in the regulator body, the pressure control chamber being in fluid communication with the regulator outlet;
- a regulator stem having a regulating end positioned in the pressure control chamber adjacent to the nozzle outlet, the regulating end being spaced apart from the nozzle outlet and being positioned to engage the selected fluid flow exiting the nozzle outlet, the regulator stem being moveable relative to the nozzle outlet to selectively increase or decrease the space therebetween to adjust a pressure of the selected fluid flow moving to the regulator outlet;
- a biasing member coupled to the regulator stem and positioned to react against movement of the stem away from the nozzle and biasing the stem toward the nozzle, the biasing member being adapted to block the regulator stem from directly engaging the nozzle;
- a stem holding member engaging a mounting end of the stem, the holding member having a threaded shaft;
- an adjustment shaft having internal and external threads forming dual concentric threads, the external threads of the adjustment shaft rotatably engaging the regulating body in the threaded aperture in the regulator body with the external threads having a first pitch, the internal threads threadably engaging the stem holding member and having a second pitch different than the first pitch, the internal and external threads having the same directional orientation, the adjustment shaft having an engagement end portion spaced apart from the internal and external threads; and
- a drive mechanism connected to the engagement portion of the adjustment shaft, the drive mechanism being rotatable to rotate the adjustment shaft to cause attenuated movement of the adjustment shaft relative to the regulator body and to move the regulator stem relative to the nozzle to control the pressure of the fluid flow moving to the outlet.

35. The pressure regulator assembly of claim 34 wherein the internal and external threads each have a threads-per-inch count, and the threads-per-inch count of the internal threads is one greater than the threads-per-inch count of the external threads.

* * * * *